United States Patent
Moszner et al.

(10) Patent No.: US 12,043,683 B2
(45) Date of Patent: Jul. 23, 2024

(54) DENTAL MATERIALS BASED ON REDOX SYSTEMS WITH OLIGOMERIC CUMENE HYDROPEROXIDE DERIVATIVES

(71) Applicants: Ivoclar Vivadent AG, Schaan (LI); Université Montpellier, Montpellier (FR); Centre National de la Recherche Scientifique, Paris (FR); Ecole Nationale Supérieure de Chimie de Montpellier, Montpellier (FR)

(72) Inventors: Norbert Moszner, Grossschwabhausen/OT Hohlstedt (DE); Yohann Catel, Sevelen (CH); Jörg Angermann, Sargans (CH); Jean-Jacques Robin, Clapiers (FR); Paul Morandi, Chaunay (FR); Sophie Monge-Darcos, Viols le Fort (FR)

(73) Assignees: Ivoclar Vivadent AG, Schaan (LI); Université Montpellier, Montpellier (FR); Centre National de la Recherche Scientifique, Paris (FR); Ecole Nationale Supérieure de Chimie Montpellier, Montpellier (FR)

(*) Notice: Subject to any disclaimer, the term of this patent is extended or adjusted under 35 U.S.C. 154(b) by 0 days.

(21) Appl. No.: 17/664,667

(22) Filed: May 24, 2022

(65) Prior Publication Data
US 2023/0002531 A1 Jan. 5, 2023

(30) Foreign Application Priority Data
May 26, 2021 (EP) .................................. 21315089

(51) Int. Cl.
| | |
|---|---|
| C08F 222/24 | (2006.01) |
| A61K 6/17 | (2020.01) |
| A61K 6/71 | (2020.01) |
| A61K 6/79 | (2020.01) |
| A61K 6/816 | (2020.01) |
| A61K 6/818 | (2020.01) |
| A61K 6/887 | (2020.01) |
| C08F 4/40 | (2006.01) |

(52) U.S. Cl.
CPC ............ *C08F 222/24* (2013.01); *A61K 6/17* (2020.01); *A61K 6/71* (2020.01); *A61K 6/79* (2020.01); *A61K 6/816* (2020.01); *A61K 6/818* (2020.01); *A61K 6/887* (2020.01); *C08F 4/40* (2013.01)

(58) Field of Classification Search
CPC ....................................................... A61K 6/61
See application file for complete search history.

(56) References Cited

U.S. PATENT DOCUMENTS

| | | | |
|---|---|---|---|
| 3,991,008 A | 11/1976 | Temin et al. | |
| 5,043,142 A * | 8/1991 | Ichikawa ................. | C12Q 1/28 436/166 |
| 7,275,932 B2 | 10/2007 | Jin et al. | |
| 7,498,367 B2 | 3/2009 | Qian | |
| 8,247,470 B2 | 8/2012 | Yarimizu et al. | |
| 11,357,709 B2 * | 6/2022 | Moszner ................. | A61K 6/816 |
| 2007/0040151 A1 | 2/2007 | Utterodt et al. | |
| 2007/0100019 A1 | 5/2007 | Sun | |
| 2010/0311864 A1 | 12/2010 | Arita et al. | |
| 2020/0253837 A1 | 8/2020 | Moszner et al. | |

FOREIGN PATENT DOCUMENTS

EP 0250090 A2 12/1987

* cited by examiner

*Primary Examiner* — Michael F Pepitone
(74) *Attorney, Agent, or Firm* — Ann M. Knab; Thad McMurray

(57) ABSTRACT

Cumene hydroperoxide oligomer according to Formula (I):

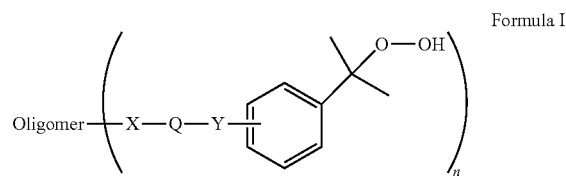

Formula I in which OLIGOMER is a homo- or copolymer chain, which is substituted n times by the group which is in brackets; Q is absent or is a divalent aromatic $C_6$-$C_{14}$ hydrocarbon radical or an aliphatic, linear or branched $C_1$-$C_{14}$ hydrocarbon radical, which can be interrupted by one or more S and/or O atoms and/or —O—CO—NR$^1$— and which can be substituted by one or more substituents; X, Y independently of each other in each case are absent, —O—, —COO—; —CONR$^3$— or —O—CO—NR$^4$—, wherein X is absent if Q is absent, and wherein the substitution on the aromatic compound is effected in position 2, 3 or 4 relative to the cumene hydroperoxide group; and n is a value from 1 to 50.

18 Claims, No Drawings

DENTAL MATERIALS BASED ON REDOX SYSTEMS WITH OLIGOMERIC CUMENE HYDROPEROXIDE DERIVATIVES

CROSS-REFERENCE TO RELATED APPLICATIONS

This application claims priority to European Patent Application No. 21315089.9 filed on May 26, 2021, the disclosure of which is incorporated herein by reference in its entirety.

TECHNICAL FIELD

The present invention relates to radically polymerizable compositions with a cumene hydroperoxide redox initiator system which contains oligomeric cumene hydroperoxide derivatives. The compositions are particularly suitable as dental materials, for example as prosthesis materials, cements, adhesives and composites for direct fillings.

BACKGROUND

The main areas of use of polymers in the dental field are removable prosthetics (e.g., teeth and prosthesis base materials) and fixed prosthetics (e.g., veneering materials, crowns or cements), filling materials (e.g., direct or indirect filling composites, luting cements or adhesives) and auxiliary materials (e.g., impression materials). The polymers are usually obtained by radical polymerization of suitable compositions which contain a polymerizable organic matrix, usually a mixture of monomers, initiator components and stabilizers.

Methyl methacrylate (MMA) (prosthesis materials), mixtures of functionalized monomers, such as e.g., 2-hydroxyethyl methacrylate (HEMA), or acid-group-containing adhesive monomers, such as e.g., 10-methacryloyloxydecyl dihydrogen phosphate (MDP), with dimethacrylates (adhesives) or mixtures which contain exclusively dimethacrylates (composite cements and filling composites) are usually used as monomers. Dimethacrylates often used are 2,2-bis[4-(2-hydroxy-3-methacryloyloxypropyl)phenyl]propane (bis-GMA) and 1,6-bis-[2-methacryloyloxyethoxycarbonylamino]-2,2,4-trimethylhexane (UDMA), which have a high viscosity and result in polymerizates with very good mechanical properties.

Above all, triethylene glycol dimethacrylate (TEGDMA), 1,10-decanediol dimethacrylate ($D_3MA$) or bis(3-methacryloyloxymethyl)tricyclo-[5.2.1.02.6]decane (DCP) are used as reactive diluents.

Methacrylate-based dental materials are cured by radical polymerization, wherein radical photoinitiators (light curing, direct filling composites and adhesives), thermal initiators (indirect composites or prosthesis materials) or redox initiator systems (composite cements) are used depending on the area of use. Moreover, the combination of photoinitiators with redox initiators, e.g., in the case of fillings of deep cavities, is known.

Redox systems are used above all when there is the risk of incomplete curing, e.g., because of a low monomer reactivity in the case of prosthesis materials or because of insufficient irradiation in the case of luting cements.

In order to guarantee a sufficient storage stability of the materials, materials based on redox initiators are usually used as so-called two-component systems (2C systems), wherein the oxidant (peroxide or hydroperoxide) and the reducing agent (amines, sulfinic acids, barbiturates, thiourea etc.) are incorporated into two separate components of the material. These components are mixed with each other shortly before use.

For a long time, redox initiator systems which are based on a mixture of dibenzoyl peroxide (DBPO) with tertiary aromatic amines, such as e.g., N,N-diethanol-p-toluidine (DEPT), N,N-dimethyl-sym.-xylidine (DMSX) or N,N-diethyl-3,5-di-tert.-butylaniline (DABA), have primarily been used for dental composite cements. Due to the limited thermal stability of DBPO, materials based on it must be stored in a refrigerator. A further disadvantage of such DBPO/amine systems is the discolorations which are caused by a slow oxidation of the amines. Moreover, the radical formation in the case of DBPO/amine-based redox initiator systems is impaired by acids and thus also by acidic monomers, which are normally used for the preparation of enamel-dentine adhesives. The amine component is protonated by an acid-base reaction and thereby deactivated.

The above disadvantages can be partially overcome with hydroperoxide redox initiator systems, because no tertiary amines are needed as reducing agent.

Moreover, hydroperoxides are more thermally stable than peroxides. Cumene hydroperoxide has, for example, a 10-hour half-life temperature $T_{1/2}$ of 158° C.; the 10-hour half-life temperature $T_{1/2}$ of DBPO is only 73° C.

DE 26 35 595 C2 and corresponding U.S. Pat. No. 3,991,008, which US patent is hereby incorporated by reference in its entirety, disclose polymerizable dental filling compounds which contain a substituted thiourea reducing agent in combination with a hydroperoxide oxidant as initiator system. The materials are said to have an improved colour stability, an excellent cure rate and an improved shelf life.

EP 1693046B1 and corresponding U.S. Pat. No. 7,498,367, which US patent is hereby incorporated by reference in its entirety, disclose dental cements and core build-up materials which contain a (2-pyridyl)-2-thiourea derivative in combination with a hydroperoxide, in which the hydroperoxide group is bonded to a tertiary carbon atom.

WO 2007/016508 A1 and corresponding US 20070100019, which US patent application is hereby incorporated by reference in its entirety, disclose a polymerizable dental composition which contains a thiourea derivative in combination with a hydroperoxide as initiator system. The composition does not contain monomers with acid groups.

According to EP 1754465B1, and corresponding US 20070040151, which US patent application is hereby incorporated by reference in its entirety, the reactivity of the cumene hydroperoxide/acetylthiourea system can be increased by the addition of soluble copper compounds.

U.S. Pat. No. 7,275,932 B2, which US patent is hereby incorporated by reference in its entirety, proposes the use of hydroperoxides and thiourea derivatives in combination with an acidic compound as accelerator. Preferred acidic compounds are acid-group-containing acrylates and methacrylates such as e.g., methacrylic acid.

EP 2233544 A1 and corresponding U.S. Pat. No. 8,247,470B2, which US patent is hereby incorporated by reference in its entirety, and EP 2258336 A1 and corresponding US 20100311864, which US patent application is hereby incorporated by reference in its entirety, disclose dental materials which contain a hydroperoxide and a thiourea derivative in combination with a vanadium compound as accelerator.

A disadvantage of cumene hydroperoxide is its typically aromatic odour, which is evocative of xylenes and toluene and is above all perceived as unpleasant in the case of materials for intraoral use.

EP 3692976 A1 and corresponding US 20200253837, which US patent application is hereby incorporated by reference in its entirety, disclose low-odour cumene hydroperoxide derivatives which are suitable as initiator for dental materials and additionally are characterized by a high storage stability.

SUMMARY

The object of the invention is to provide low-odour hydroperoxides which are suitable as initiators for radical polymerization and have a reduced risk of toxic side effects.

They are to be suitable in particular for the preparation of dental materials.

DETAILED DESCRIPTION

This object is achieved by cumene hydroperoxide (CHP) oligomers according to the following Formula (I):

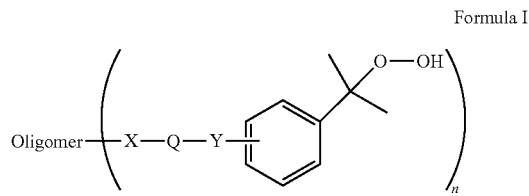

Formula I in which the variables have the following meanings:
OLIGOMER a homo- or copolymer chain, which is substituted n times by the group which is in brackets,
Q is absent, a divalent aromatic $C_6$-$C_{14}$ hydrocarbon radical or a linear or branched, aliphatic $C_1$-$C_{14}$ hydrocarbon radical, which can be interrupted by one or more S and/or O atoms and/or —O—CO—$NR^1$ and which can be unsubstituted or substituted by one or more substituents, which are preferably selected from —OH, —$OR^2$, —Cl and —Br, wherein $R^1$ is H or a $C_1$-$C_5$ alkyl radical, preferably methyl, ethyl, propyl or tert.-butyl, and $R^2$ is an aliphatic, linear or branched $C_1$-$C_1$ hydrocarbon radical,
X, Y independently of each other in each case are absent, —O—, —COO—; —$CONR^3$— or —O—CO—$NR^4$—, wherein $R^3$ and $R^4$ independently of each other in each case represent H or a $C_1$-$C_5$ alkyl radical, preferably represent H, methyl and/or ethyl, particularly preferably H, and wherein X is absent if Q is absent, and wherein the substitution on the aromatic compound is effected in position 2, 3 or 4 relative to the cumene hydroperoxide group,
n a value from 1 to 50.

All formulae shown herein extend only to those compounds which are compatible with the theory of chemical valence. The indication that a radical is interrupted e.g., by one or more 0 atoms is to be understood to mean that these atoms are inserted in each case into the carbon chain of the radical. These atoms are thus bordered on both sides by C atoms and cannot be terminal. $C_1$ radicals cannot be interrupted or branched. The groups —COO—; —$CONR^3$—, —O—CO—$NR^1$— and —O—CO—$NR^4$— can be arranged in any desired orientation. For example, —COO— represents both —CO—O— and —O—CO—. Corresponding to the usual nomenclature, by aromatic hydrocarbon radicals is also meant those radicals which contain aromatic and non-aromatic groups.

The variables preferably have the following meanings:
OLIGOMER a (meth)acrylate- or styrene-based copolymer chain, which is substituted n times by the group which is in brackets,
Q a divalent aliphatic, linear or branched $C_1$-$C_{10}$ radical, which can be interrupted by 1 to 3 O atoms and can carry 1 to 3 OH or $OR^2$ substituents, wherein $R^2$ is preferably an aliphatic, linear or branched $C_1$-$C_5$ alkyl radical,
X, Y independently of each other in each case are absent, an ether, ester or urethane group, wherein the substitution on the aromatic compound is effected in position 4, and
n a value from 5 to 20.

The preferred, particularly preferred and quite particularly preferred definitions given for the individual variables can be selected in each case independently of each other.

Compounds in which all the variables have the preferred, particularly preferred and quite particularly preferred definitions are naturally particularly suitable according to the invention.

A direct synthesis and polymerization of cumene hydroperoxide-group-containing monomers is only possible with difficulty because of their low stability. The CHP oligomers of Formula I according to the invention are therefore preferably prepared by a three-stage synthesis.

In the $1^{st}$ stage, first of all, polymerizable isopropylbenzene monomers are prepared through esterification e.g., of a COOH-functionalized isopropylbenzene derivative, preferably 4-isopropylbenzoic acid, with an OH-functionalized monomer. OH-functionalized monomers with radically polymerizable styrene groups and preferably (meth)acrylate groups as polymerization group (PG), such as e.g., 2-hydroxyethyl methacrylate (HEMA), are preferred:

Generally:

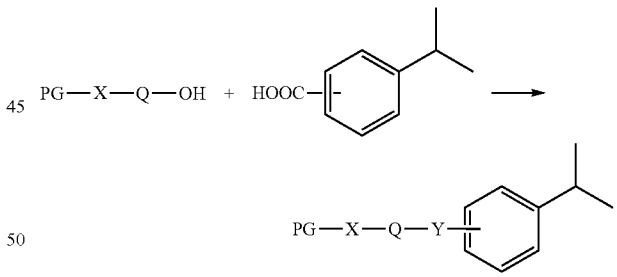

Specific Example

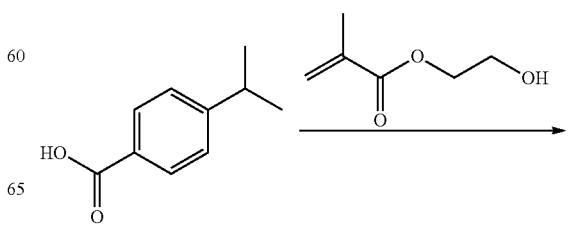

-continued

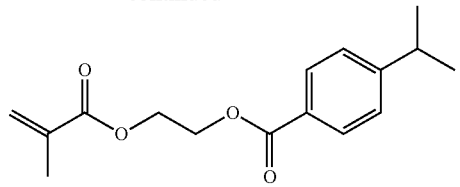

In the 2$^{nd}$ stage, the polymerizable isopropylbenzene monomer obtained in this way is homo- or copolymerized using the known methods of radical polymerization in the presence of an initiator, such as e.g., AIBN (azobisisobutyronitrile). During the homopolymerization, a homopolymer with isopropylbenzene monomer repeating units, which has a degree of polymerization of n, forms. A chain regulator, e.g., a mercaptan R—SH, is preferably used to control the molar mass. In this case, the polymer chain carries an end group (EG) with the formula —S—R:

Generally, homopolymerization:

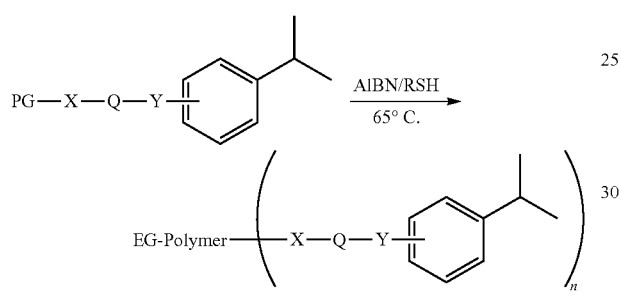

Specific Example

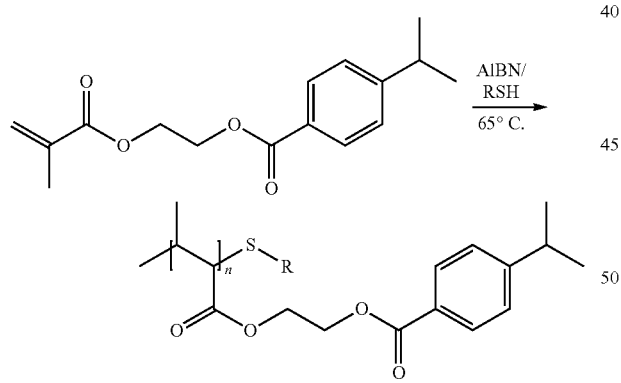

According to a preferred embodiment, the polymerizable isopropylbenzene monomer is copolymerized with one or more radically polymerizable comonomers. The polymerizable isopropylbenzene monomer and the comonomers used preferably contain (meth)acrylate groups and thus form poly(meth)acrylate chains during the polymerization, which are substituted by isopropylbenzene groups and ester groups —COOR'. The arrangement of the monomer building blocks in the copolymer chain can be alternating, block or preferably statistical. A radical copolymerization usually results in a statistical arrangement of the monomer building blocks. Block copolymers are obtainable using known methods of controlled radical polymerization. The composition of the copolymers formed is determined above all by the composition of the comonomer mixture used. A chain regulator, such as e.g., a mercaptan R—SH, is preferably used here too:

Generally, copolymerization:

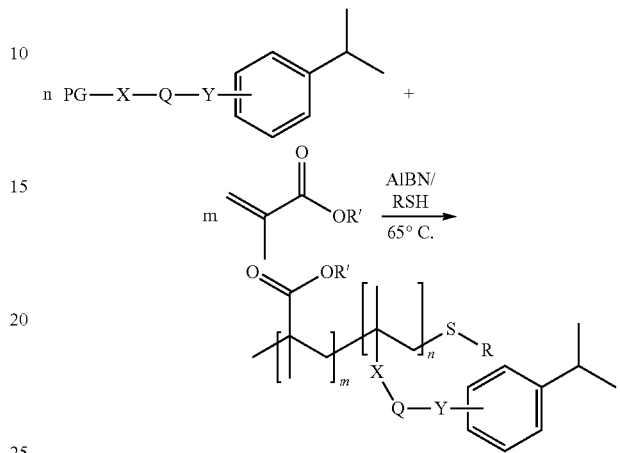

Specific Example: Copolymerization with Methyl Methacrylate (MMA)

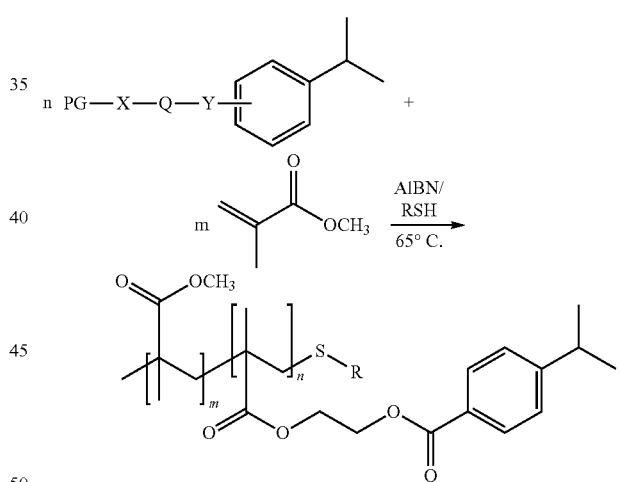

In the 3$^{rd}$ stage, the homo- or copolymers obtained in the 2$^{nd}$ stage are then converted, in a polymer-analogous reaction, into the CHP oligomers of Formula I according to the invention by oxidation of the isopropyl groups, e.g., with atmospheric oxygen in the presence of AIBN and N-hydroxyphthalimide (NHPI), without changing the degree of polymerization.

Generally:

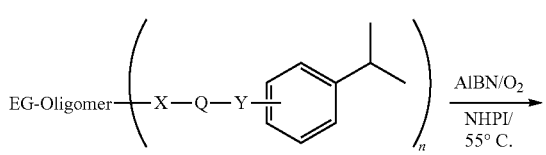

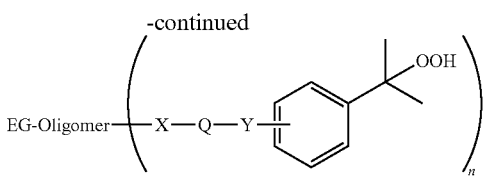

Specific Example

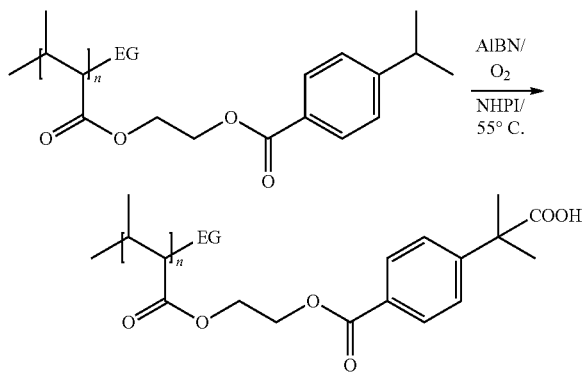

The oxidation of the isopropyl groups to hydroperoxide groups does not proceed completely, with the result that the oligomers may still contain a small quantity of isopropyl groups. Oligomers in which at least 70%, particularly preferably at least 75%, quite particularly preferably at least 80% and most preferably at least 85% of the isopropyl groups have been converted to hydroperoxide groups are preferred.

If the starting polymer contains a thioether end group, this is preferably converted into a sulfone group before the oxidation of the isopropylbenzene groups, preferably by reaction with magnesium monoperoxyphthalate hexahydrate.

Preferred comonomers for the synthesis of the CHP oligomers of Formula I according to the invention are (meth)acrylates with the general formula $H_2C=CR'''-COOR'$, in which $R'''$ is H or methyl, and $R'$ is a linear or branched $C_1$-$C_{10}$ alkyl radical, which can be unsubstituted or substituted by one or more functional groups, preferably —OH, —COOH and/or —$C_1$, benzyl or furfuryl. Particularly preferred comonomers are methyl, ethyl, propyl, butyl, hexyl, 2-hydroxyethyl, hydroxypropyl, benzyl, furfuryl, isobornyl or 2-ethylhexyl (meth)acrylate and mixtures thereof, wherein in all cases the methacrylates are quite particularly preferred. Through the use of comonomers, e.g., the solubility of the CHP oligomers of Formula I in monomer mixtures can be improved.

Isopropylbenzene monomers and comonomers are preferably used in a molar ratio of from 0.1 to 0.9, particularly preferably of from 0.5 to 0.9. As the content of cumene hydroperoxide groups in the CHP oligomers of Formula I increases, the quantity of CHP oligomers in radically polymerizable compositions based on them that is necessary for the initiation of the radical polymerization decreases accordingly.

CHP co-oligomers can also be obtained by copolymerizing different isopropylbenzene monomers in stage 2.

According to another embodiment of the invention, the CHP oligomers of Formula I according to the invention are prepared in the $1^{st}$ stage by preparing copolymers with suitable reactive side groups, such as hydroxyl or carboxyl groups, preferably by radical copolymerization of 2-hydroxyethyl (meth)acrylate or (meth)acrylic acid with other mono(meth)acrylates. In the $2^{nd}$ stage, the OH— or COOH-functionalized copolymers obtained in this way are then esterified by a polymer-analogous reaction with a corresponding isopropylbenzene derivative, e.g., with 4-isopropylbenzoic acid in the case of OH— group-containing polymers or 4-isopropylphenol in the case of COOH-containing polymers. In the $3^{rd}$ stage, the homo- or copolymers prepared in the $2^{nd}$ stage are converted into the CHP oligomers of Formula I according to the invention by oxidation of the isopropyl groups, e.g., by reaction with atmospheric oxygen in the presence of AIBN and N-hydroxyphthalimide (NHPI).

According to a further embodiment of the invention, in the $1^{st}$ stage isocyanate-group-containing copolymers are prepared, preferably by radical copolymerization of (meth)acrylates with 2-isocyanatoethyl methacrylate, which are then reacted in the $2^{nd}$ stage e.g., with p-isopropylbenzyl alcohol. In the $3^{rd}$ stage, the CHP oligomers of Formula I according to the invention are obtained after oxidation of the isopropyl groups, e.g., with atmospheric oxygen in the presence of AIBN and N-hydroxyphthalimide (NHPI).

The oligomers according to the invention are preferably prepared using a chain transfer agent to limit the chain length. Chain transfer agents are also called chain regulators. Chain regulators preferred according to the invention are mercaptans, in particular mercaptans of the formula R—$(SH)_p$, in which R is a linear or branched aliphatic $C_1$-$C_{15}$ hydrocarbon radical, which can be interrupted by one or more S and/or O atoms and/or —COO— and can be unsubstituted or substituted by one or more Br and/or $C_1$ atoms and/or OH or COOH groups, or an aromatic $C_6$-$C_{12}$ hydrocarbon radical, and p is 1 or 2, preferably 1. R is preferably a branched and particularly preferably a linear $C_2$-$C_{15}$ alkyl radical, which can be substituted by functional groups, in particular —Br, —$C_1$, —OH and/or —COOH, and which is preferably not substituted. Particularly preferred mercaptans are lauryl mercaptan (1-dodecanethiol, DDT), 2-mercaptoethanol, 3-mercaptopropanol, 3-mercapto-2-butanol, 2-mercapto-3-butanol, 3-mercapto-2-methyl-butan-1-ol, 3-mercapto-3-methyl-hexan-1-ol, 3-mercaptohexanol, 2-mercaptoacetic acid, 3-mercaptopropionic acid, 4-methylbenzenethiol, isooctyl 3-mercaptopropionate, tert-nonylmercaptan, 4,4'-thiobisbenzenethiol and 1,8-dimercapto-3,6-dioxaoctane.

Further preferred chain regulators are disulfides (R—S—S—R), in particular dithiourethane disulfides, such as tetramethylthiuram disulfide and isopropylxanthic disulfide. Disulfides are also called photoiniferters because they act as photoinitiator (photoini-) during the radical photopolymerization and at the same time also take part in transfer reactions (-fer-) and termination reactions (-ter).

In addition, silanes, in particular trimethylsilane and pentamethyldisilane, as well as halogenated compounds, in particular carbon tetrachloride, carbon tetrabromide and bromotrichloromethane, can be used as chain regulator.

Chain regulators particularly preferred according to the invention are alkyl mercaptans (R—SH, wherein R is a linear $C_2$-$C_{15}$ alkyl radical), mercaptoethanol and mercaptoacetic acid.

The degree of polymerization of the CHP oligomers according to the invention results from the synthesis. The composition of co-oligomers can be determined by $^1$H-NMR spectroscopy, and the peroxide content n can be established by $^1$H-NMR spectroscopy or by titration.

The CHP oligomers of Formula I according to the invention preferably have a number-average molar mass of from 500 to 10,000 g/mol, particularly preferably of from 800 to 6,000 g/mol and quite particularly preferably of from 1,000 to 3,000 g/mol. A lower molar mass results in a low solution viscosity, which is advantageous when used in resins, cements or composites.

Unless otherwise stated, herein the molar mass of oligomers and polymers is the number-average molar mass, the absolute values of which can be determined using the known methods of freezing point depression (cryoscopy), boiling point elevation (ebullioscopy) or from the decrease in the vapour pressure (vapour pressure osmometry). The number-average molar mass of oligomers and polymers is preferably determined by means of gel permeation chromatography (GPC). This is a relative method in which the molecules are separated on the basis of their size, more specifically on the basis of their hydrodynamic volume. The absolute molar mass is determined through calibration with known standards.

CHP oligomers preferred according to the invention can be represented by the following Formula II,

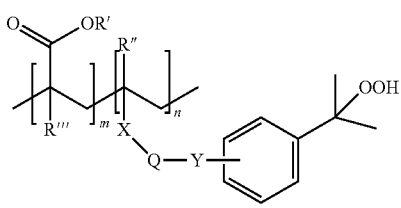

Formula II in which
- R' is a linear or branched $C_1$-$C_{10}$ alkyl radical, which can be substituted by one or more functional groups, in particular —OH, —COCH and/or —$C_1$, or is preferably unsubstituted, or a cyclic $C_4$-$C_{10}$ alkyl radical, a heterocyclic or isocyclic aromatic $C_4$-$C_6$ hydrocarbon radical,
- R',R''' independently of each other in each case are H or methyl,
- m is a number from 0 to 30, preferably 1 to 20,
- n is a number from 1 to 50, preferably 2 to 30, and
- the remaining variables have the meanings named above.

In homopolymers m=0 and in copolymers m≥1. The ratio of n to m preferably lies in a range of from 0.1 to 0.9, particularly preferably 0.5 to 0.9. The sum of n+m is preferably greater than 10 and less than 100.

In accordance with general technical knowledge, the chain length of the polymer chains varies and n and m are thus averages (number averages) in all cases.

In Formulae I and II, the end groups of the polymer chain are not specified in accordance with the usual conventions. The chain transfer proceeds according to the following diagram:

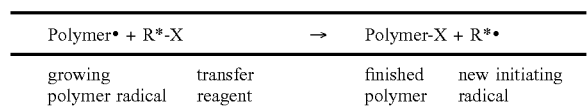

When chain regulators are used, chains with the end groups R* and X are thus obtained. Chain regulators preferred according to the invention are mercaptans R—SH (R*=R—S—; X=H), with the result that polymer chains are obtained which carry an H atom or an R—S— group as end groups, wherein the R—S— groups are preferably oxidized to sulfoxide (—SO—R) and in particular sulfone (—SO$_2$R) groups. Mercaptans with two mercapto groups R—(SH)$_2$ correspondingly yield end groups with the formula HS—R—S—.

In an analogous manner, disulfides result in end groups with the formula R—S—. Carbon tetrachloride (CCl$_4$), carbon tetrabromide (CBr$_4$) and bromotrichloromethane (CBrCl$_3$) result in the following end groups: —CCl$_3$, —CBr$_3$ and —CCl$_3$.

If no chain regulators are used for the preparation of the oligomers according to the invention, the end group of the oligomers is determined by the initiator used for the polymerization. Initiators preferred according to the invention are azobis(isobutyronitrile) (AIBN), diperoxides, in particular dibenzoyl peroxide and di-tert-butyl peroxide, and peroxodisulfates, in particular potassium peroxodisulfate K$_2$S$_2$O$_8$, sodium peroxodisulfate Na$_2$S$_2$O$_8$. These initiators result in the following end groups: dibenzoyl peroxide: C$_6$H$_5$—(CO)—O—; di-tert-butyl peroxide: C$_4$H$_9$—O—; K$_2$S$_2$O$_8$: KSO$_4$, Na$_2$S$_2$O$_8$:NaSO$_4$. In accordance with general technical knowledge, end groups are also formed through combination and disproportionation of polymer chains.

Preferred CHP oligomers which are obtained using mercaptans as chain regulator can be represented by the following Formula IIa,

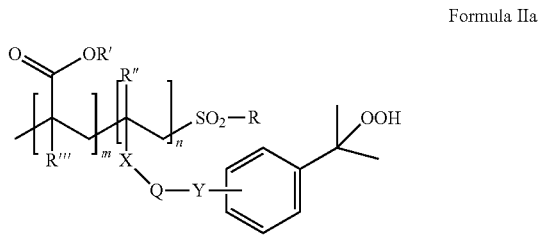

Formula IIa in which
- R is a branched or preferably linear $C_2$-$C_{15}$ alkyl radical, which can be substituted by one or more functional groups, in particular —Br, —$C_1$, —OH and/or —COCH, or is preferably unsubstituted,
- R' is a linear or branched $C_1$-$C_{10}$ alkyl radical, which can be substituted by one or more functional groups, in particular —OH, —COOH and/or —$C_1$, or is preferably unsubstituted, or a cyclic $C_4$-$C_{10}$ alkyl radical, a heterocyclic or isocyclic aromatic $C_4$-$C_6$ hydrocarbon radical,
- R',R''' independently of each other in each case are H or methyl,
- m is a number from 0 to 30, preferably 1 to 20,
- n is a number from 1 to 50, preferably 2 to 30, and
- the remaining variables have the meanings named above.

In Formulae II and IIa, the group

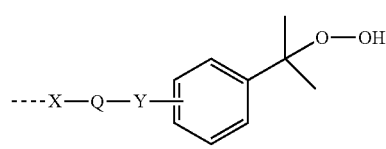

preferably has one of the following structures:

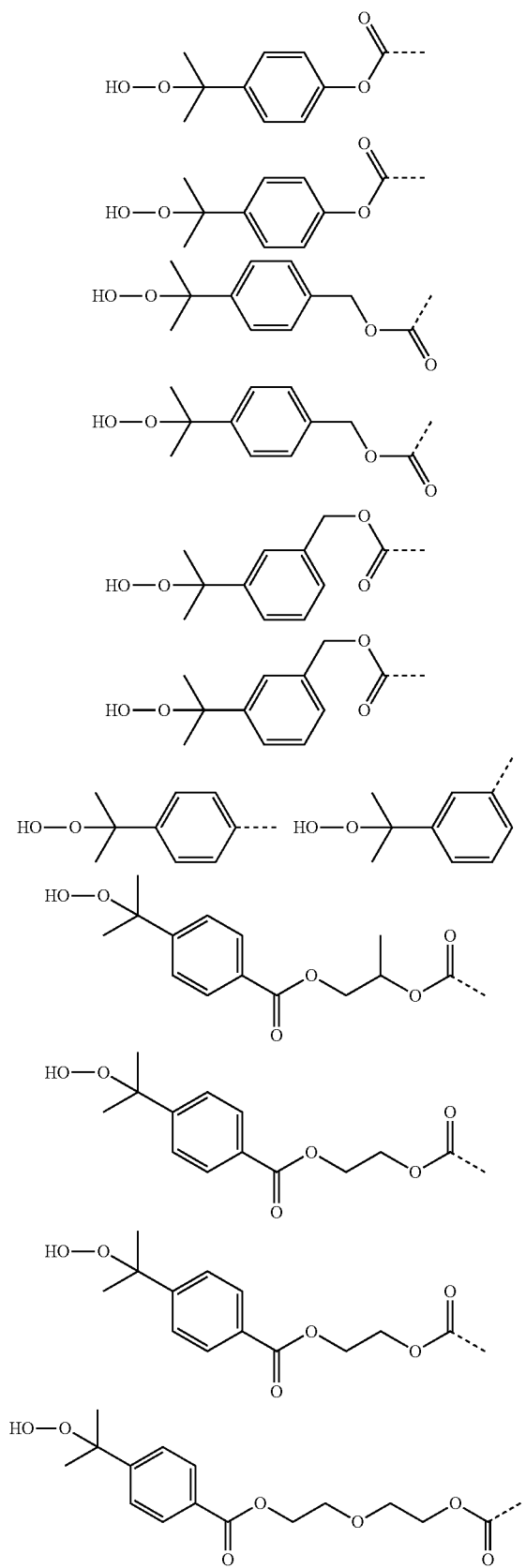

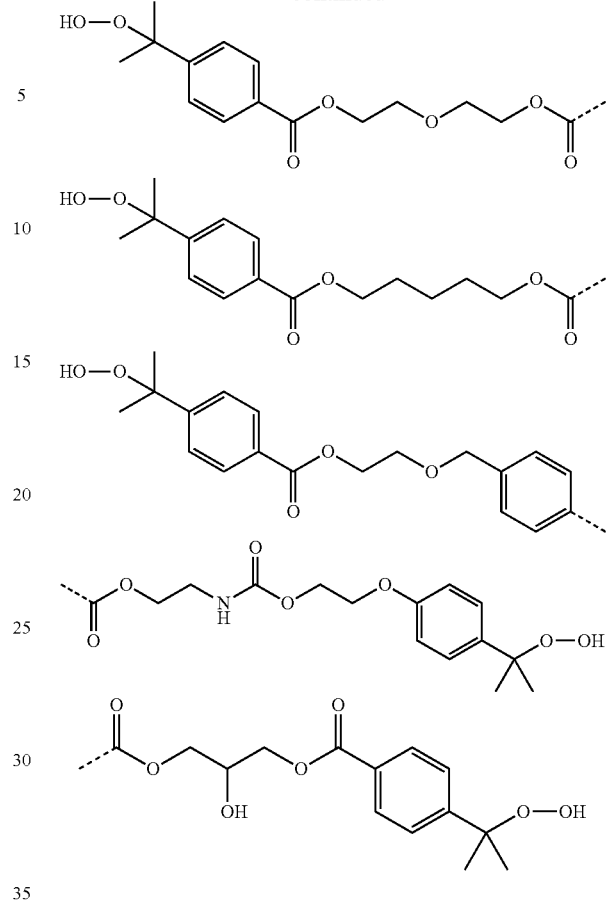

The CHP oligomers of Formula I have a high storage stability at room temperature, are odour-free, possess a low solubility in water and can be used as hydroperoxide component in redox initiator systems for radically polymerizable compositions, in particular in redox initiator systems for dental compositions. A particular advantage of the oligomeric or polymeric compounds of Formula I according to the invention is that they are not released from the cured materials after the polymerization, which is a considerable advantage with regard to possible toxic side effects for dental and other medical applications. Radically polymerizable compositions which contain at least one CHP oligomer of Formula I are likewise a subject-matter of the invention.

The compositions according to the invention preferably contain at least one thiourea derivative as accelerator in addition to the CHP oligomer of Formula (I). Thiourea derivatives preferred according to the invention are the compounds listed in paragraph [0009] in EP 1 754 465 A1. Particularly preferred thiourea derivatives are acetyl-, allyl-, pyridyl- and phenylthiourea, hexanoylthiourea and mixtures thereof. Acetylthiourea (ATU) is quite particularly preferred.

Thiourea derivatives with the Formula III are further preferred

Formula III

in which

X' is H or Y',

Y' is an alkyl radical with 1 to 8 carbon atoms, a cycloalkyl radical with 5 or 6 carbon atoms, a chlorine-, hydroxy- or mercapto-substituted alkyl radical with 1 to 8 carbon atoms, an alkenyl radical with 3 to 4 carbon atoms, an aryl radical with 6 to 8 carbon atoms, a chlorine-, hydroxy-, methoxy- or sulfonyl-substituted phenyl radical, an acyl radical with 2 to 8 carbon atoms, a chlorine- or methoxy-substituted acyl radical, an aralkyl radical with 7 to 8 carbon atoms or a chlorine- or methoxy-substituted aralkyl radical, and Z' is $NH_2$, NHX' or $NX'_2$.

In addition, cyclic thiourea derivatives are further preferred. By cyclic thiourea derivatives is here meant those compounds in which the nitrogen atoms of the thiourea group form a heterocyclic ring system together with the carbon atom lying in between and further carbon atoms. Cyclic thiourea derivatives of Formula (IV) are preferred:

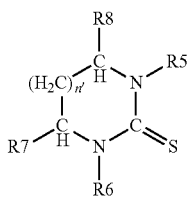

Formula IV in which:

$R^5$, $R^6$ in each case are H or a $C_1$-$C_4$ alkyl radical, wherein at least one of these radicals is H;

$R^7$, $R^8$ independently of each other in each case are H, a $C_1$-$C_4$ alkyl radical or a $C_1$-$C_4$ alkoxy radical or, together with the carbon atoms to which they are bonded and the carbon atom lying in between, form a six-membered, carbocyclic, aliphatic or aromatic ring, which can be substituted by one or more, preferably 1 or 2, $C_1$-$C_4$ alkyl radicals and/or $C_1$-$C_4$ alkoxy radicals;

n' is 0, 1, 2 or 3, preferably 0 or 1.

The variables of Formula IV preferably have the following meanings:

$R^5$, $R^6$ in each case H or a $C_1$-$C_2$ alkyl radical, preferably H or methyl, wherein at least one of these radicals is H;

$R^7$, $R^8$ in each case H, a $C_1$-$C_2$ alkyl radical, preferably methyl, a $C_1$-$C_2$ alkoxy radical, preferably methoxy, or, together with the carbon atoms to which they are bonded and the carbon atom lying in between, form a benzene ring, which can be substituted by a $C_1$-$C_2$ alkyl radical, preferably methyl, or a $C_1$-$C_2$ alkoxy radical, preferably methoxy;

n' 0 or 1.

The variables of Formula IV particularly preferably have the following meanings:

$R^5$, $R^6$ in each case H or methyl, wherein at least one of these radicals is H;

$R^7$, $R^8$ in each case H, a $C_1$-$C_2$ alkyl radical, preferably methyl, or a $C_1$-$C_2$ alkoxy radical, preferably methoxy, and n' 1, or $R^5$, $R^6$ in each case H or methyl, wherein at least one of these radicals is H;

$R^7$, $R^8$ form, together with the carbon atoms to which they are bonded and the carbon atom lying in between, a benzene ring, which can be substituted by a $C_1$-$C_2$ alkyl radical, preferably methyl, or a $C_1$-$C_2$ alkoxy radical, preferably methoxy, and n' 0.

In all cases, Formula IV also comprises the corresponding isothiourea derivatives. 3,4,5,6-Tetrahydro-2-pyrimidinethiol (1), 2-imidazolidinethione (2), 2-mercaptobenzimidazole (4), 1-methyl-1H-benzimidazole-2-thiol, 2-mercapto-1-methylimidazole and 2-mercapto-5-methoxybenzimidazole are particularly preferred.

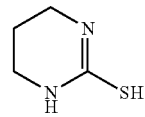

(1)

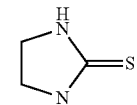

(2)

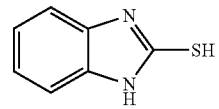

(4)

According to a quite particularly preferred embodiment of the invention, a combination of at least one cyclic thiourea derivative and at least one acyclic thiourea derivative is used as accelerator.

According to a further preferred embodiment, the compositions according to the invention additionally contain at least one transition metal compound in addition to at least one CHP oligomer of Formula I and at least one thiourea derivative. It has been found that the addition of a transition metal compound yields materials which have significantly improved mechanical properties after curing.

Transition metal compounds preferred according to the invention are compounds which are derived from those transition metals which have at least two stable oxidation states. Compounds of the elements copper, iron, cobalt, nickel and manganese are particularly preferred. These metals have the following stable oxidation states: Cu(I)/Cu(II), Fe(II)/Fe(III), Co(II)/Co(III), Ni(II)/Ni(III), Mn(II)/Mn(III). Compositions which contain at least one copper compound are particularly preferred.

The transition metals are preferably used in the form of their salts. Preferred salts are the nitrates, acetates, 2-ethylhexanoates and halides, wherein chlorides are particularly preferred.

The transition metals can furthermore advantageously be used in complexed form, wherein complexes with chelate-forming ligands are particularly preferred. Preferred simple ligands for complexing the transition metals are 2-ethylhexanoate and THF. Preferred chelate-forming ligands are 2-(2-aminoethylamino)ethanol, aliphatic amines, particularly preferably 1,1,4,7,10,10-hexamethyltriethylenetetramine (HMTETA), N,N,N',N'',N''-pentamethyldiethylenetriamine (PMDETA), tris[2-(dimethylamino)ethyl]amine ($Me_6TREN$), N,N,N',N'-tetramethylethylenediamine (TMEDA), 1,4,8,11-tetraaza-1,4,8,11-tetramethylcyclotetradecane (Me4CYCLAM), diethylenetriamine (DETA), triethylenetetramine (TETA) and 1,4,8,11-tetraazacyclotetradecane (CYCLAM); pyridine-containing ligands, particularly preferably N,N,N',N'-tetrakis(2-pyridylmethyl) ethylenediamine (TPEN), N,N-bis(2-pyridylmethyl)amine (BPMA), N,N-bis(2-pyridylmethyl)octylamine (BPMOA), 2,2'-bipyridine and 8-hydroxyquinoline. Quite particularly preferred ligands are acetylacetone, dimethylglyoxime, 8-hydroxyquinoline, 2,2'-bipyridine and 1,10-phenanthroline.

In the case of electrically neutral ligands, the charge of the transition metal ions must be balanced by suitable counterions. For this, the above-named ions which are used to form salts are considered in particular, wherein acetates and chlorides are particularly preferred. Chlorides and complexes are characterized by a relatively good solubility in monomers which are used to prepare dental materials.

Instead of the transition metal complexes, non-complex salts of the transition metals in combination with complex-forming organic compounds can be used to prepare compositions according to the invention, preferably in combination with the above-named chelate-forming compounds. The organic ligands form the catalytically active complexes when mixed with the transition metal salts. The use of such combinations of transition metal salts and organic ligands is preferred.

Transition metal compounds of the metals copper, iron, cobalt and nickel are preferred.

Preferred copper salts are CuCl, CuBr, $CuCl_2$, $CuBr_2$, $CuI_2$, Cu(II) carboxylates (e.g., of acetic acid or 2-ethylhexanoic acid). Preferred copper complexes are complexes with the ligands acetylacetone, phenanthroline (e.g., 1,10-phenanthroline (phen)), the aliphatic amines, such as e.g., 1,1,4,7,10,10-hexamethyltriethylenetetramine (HMTETA), N,N,N',N'',N''-pentamethyldiethylenetriamine (PMDETA), tris[2-(dimethylamino)ethyl]amine ($Me_6TREN$).

Preferred iron salts are $FeCl_3$, $FeBr_2$ and $FeCl_2$. Preferred iron complexes are complexes with the ligands acetylacetone, triphenylphosphine, 4,4'-di(5-nonyl)-2,2'-bipyridine (dNbpy) or 1,3-diisopropyl-4,5-dimethylimidazol-2-ylidene (PrIlm). The complexes $Fe(acac)_2$ and $FeCl_2(PPh_3)_2$ are quite particularly preferred.

Preferred nickel salts are $NiBr_2$ and $NiCl_2$, preferred nickel complexes are nickel acetylacetonate and $NiBr_2(PPh_3)_2$.

In all cases, those complexes in which the respective transition metal is present in its most stable oxidation state are preferred. Complexes of $Cu^{2+}$, $Fe^{3+}$, $Ni^{2+}$ and $Co^{3+}$ are thus preferred.

According to the invention, copper compounds, copper complexes and in particular mixtures of copper salts and complexing organic ligands are particularly preferred.

Compositions which contain at least one CHP oligomer of Formula I, at least one thiourea derivative and at least one transition metal compound, wherein these components are preferably in each case selected from the above-defined preferred and particularly preferred substances, are quite particularly preferred.

The CHP oligomer or oligomers of Formula I are preferably used in a quantity of from 0.5 to 10 wt.-%, particularly preferably 1.0 to 8.0 wt.-% and quite particularly preferably 1.5 to 5.0 wt.-%.

The thiourea derivative or derivatives are preferably used in a quantity of from 0.01 to 5 wt.-%, particularly preferably 0.05 to 2.0 wt.-%.

The transition metal compound is, where applicable, preferably used in a quantity of from 0.0001 to 1 wt.-%, preferably 0.0005 to 0.5 wt.-% and particularly preferably 0.0007 to 0.020 wt.-%.

Unless otherwise stated, all percentages herein relate to the total mass of the composition.

According to the invention, compositions which contain at least one radically polymerizable monomer are preferred, compositions which contain at least one mono- and/or preferably multifunctional (meth)acrylate as radically polymerizable monomer are particularly preferred. By monofunctional (meth)acrylates is meant compounds with one, by multifunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates.

Materials which are to be cured intraorally preferably contain mono- and/or multifunctional methacrylates as radically polymerizable monomer.

Preferred multifunctional (meth)acrylates are bisphenol A dimethacrylate, bis-GMA 30 (an addition product of methacrylic acid and bisphenol A diglycidyl ether), ethoxylated or propoxylated bisphenol A dimethacrylate, such as e.g., the bisphenol A dimethacrylate SR-348c (Sartomer) with 3 ethoxy groups or 2,2-bis[4-(2-methacryloyloxypropoxy)phenyl]propane, UDMA (an addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), di-, tri- or tetraethylene glycol dimethacrylate, trimethylolpropane trimethacrylate, pentaerythritol tetramethacrylate as well as glycerol di- and trimethacrylate, 1,4-butanediol dimethacrylate, 1,10-decanediol dimethacrylate ($D_3MA$), bis(methacryloyloxymethyl)tricyclo-[5.2.1.0$^{2,6}$]decane (DCP), polyethylene glycol or polypropylene glycol dimethacrylates, such as e.g., polyethylene glycol 200 dimethacrylate or polyethylene glycol 400 dimethacrylate (PEG 200 DMA or PEG 400 DMA) or 1,12-dodecanediol dimethacrylate, or a mixture thereof.

Preferred monofunctional monomers are benzyl and furfuryl methacrylate, 2-phenoxyethyl methacrylate, 2-(o-biphenyloxy)ethyl methacrylate, 2-hydroxy-3-phenoxypropyl methacrylate, phenethyl methacrylate, 2-[(benzyloxycarbonyl)-amino]-ethyl methacrylate, 2-[(benzylcarbamoyl)oxy]-ethyl methacrylate, 1-phenoxypropan-2-yl methacrylate and 2-(p-cumylphenoxy)-ethyl methacrylate, tricyclodecane methacrylate, tricyclodecane methyl methacrylate and/or 2-(p-cumylphenoxy)ethyl methacrylate.

According to an embodiment, the compositions according to the invention preferably additionally contain one or more acid-group-containing radically polymerizable monomers (adhesive monomers) in addition to the above-named monomers. These give the materials self-adhesive and/or self-etching properties. Acid-group-containing monomers are therefore particularly suitable for the preparation of self-adhesive dental materials, such as e.g., luting cements.

Preferred acid-group-containing monomers are polymerizable carboxylic acids, phosphonic acids and phosphoric acid esters as well as their anhydrides. Preferred carboxylic acids and carboxylic acid anhydrides are 4-(meth)acryloyloxyethyl trimellitic acid anhydride, 10-methacryloyloxydecylmalonic acid, N-(2-hydroxy-3-methacryloyloxypropyl)-N-phenylglycine, 4-vinylbenzoic acid. Preferred phosphoric acid esters are 2-methacryloyloxyethylphenyl hydrogen phosphate, 10-methacryloyloxydecyl dihydrogen phosphate (MDP) and dipentaerythritol pentamethacryloyloxyphosphate. Preferred phosphonic acids are 4-vinylbenzyl-phosphonic acid, 2-[4-(dihydroxyphosphoryl)-2-oxa-butyl]-acrylic acid and their amides, esters, such as e.g., 2-[4-(dihydroxyphosphoryl)-2-oxa-butyl]-acrylic acid-2,4,6-trimethylphenyl ester.

Particularly preferred acid-group-containing monomers are 4-vinylbenzylphosphonic acid, 2-[4-(dihydroxyphosphoryl)-2-oxa-butyl]-acrylic acid and their amides, esters, such as e.g., 2-[4-(dihydroxyphosphoryl)-2-oxa-butyl]-acrylic acid-2,4,6-trimethylphenyl ester, (meth)acrylamide dihydrogen phosphates, such as e.g., 6-methacrylamido-hexyl or 1,3-bis(methacrylamido)-propan-2-yl dihydrogen phosphate, and mixtures thereof. These particularly preferred acid-group-containing monomers are characterized by a high hydrolytic stability.

The compositions according to the invention can advantageously additionally contain an initiator for the radical photopolymerization in addition to the initiator system according to the invention. Such compositions are dual-curing, i.e., they can be cured both chemically and by light. Preferred photoinitiators are benzophenone and benzoin as well as their derivatives, α-diketones or their derivatives, such as 9,10-phenanthrenequinone, 1-phenyl-propane-1,2-dione, diacetyl or 4,4'-dichlorobenzil. Camphorquinone (CQ) and 2,2-dimethoxy-2-phenyl-acetophenone are particularly preferably used, and α-diketones in combination with amines as reducing agent, such as e.g., 4-(dimethylamino)benzoic acid ethyl ester (EDMAB), N,N-dimethylaminoethyl methacrylate, N,N-dimethyl-sym.-xylidine or triethanolamine, are quite particularly preferably used.

The compositions according to the invention preferably do not contain amines. Norrish type I photoinitiators are therefore particularly preferred. Norrish type I photoinitiators do not require an amine component. Preferred Norrish type I photoinitiators are acyl- or bisacylphosphine oxides, and in particular monoacyltrialkylgermanium, diacyldialkylgermanium and tetraacylgermanium compounds, such as e.g., benzoyltrimethylgermanium, dibenzoyldiethylgermanium, bis(4-methoxybenzoyl)diethylgermanium (Ivocerin®), tetrabenzoylgermanium or tetrakis(o-methylbenzoyl)germanium.

Moreover, mixtures of the different photoinitiators can also be used, such as e.g., bis(4-methoxybenzoyl)diethylgermanium or tetrakis(o-methylbenzoyl)germanium in combination with camphorquinone and 4-dimethylaminobenzoic acid ethyl ester.

The compositions according to the invention can moreover advantageously contain one or more organic or inorganic fillers. Particulate fillers are preferred. Filler-containing compositions are particularly suitable as dental luting cements or filling composites.

Preferred inorganic fillers are oxides, such as $SiO_2$, $ZrO_2$ and $TiO_2$ or mixed oxides of $SiO_2$, $ZrO_2$, ZnO and/or $TiO_2$, nanoparticulate or microfine fillers, such as fumed silica or precipitated silica, glass powders, such as quartz, glass ceramic, borosilicate glass powders or radiopaque glass powders, preferably barium or strontium aluminium silicate glasses, and radiopaque fillers, such as ytterbium trifluoride, tantalum(V) oxide, barium sulfate or mixed oxides of $SiO_2$ with ytterbium(III) oxide or tantalum(V) oxide. The compositions according to the invention can furthermore contain fibrous fillers, nanofibres, whiskers or mixtures thereof.

Preferably, the oxides have a particle size of from 0.010 to 15 μm, the nanoparticulate or microfine fillers have a particle size of from 10 to 300 nm, the glass powders have a particle size of from 0.01 to 15 μm, preferably of from 0.2 to 1.5 μm, and the radiopaque fillers have a particle size of from 0.2 to 5 μm.

Particularly preferred fillers are mixed oxides of $SiO_2$ and $ZrO_2$, with a particle size of from 10 to 300 nm, preferably 5 to 10 nm, which are obtainable e.g., by hydrolytic co-condensation of metal alkoxides, glass powders with a particle size of from 0.2 to 1.5 μm, in particular radiopaque glass powders of e.g., barium or strontium aluminium silicate glasses, and radiopaque fillers with a particle size of from 0.2 to 5 μm, in particular ytterbium trifluoride and/or mixed oxides of $SiO_2$ with ytterbium(III) oxide.

Moreover, ground prepolymers or pearl polymers (isofillers) are suitable as fillers. These can consist exclusively of organic polymers, or of organic polymers which themselves are filled with inorganic fillers. The type of the inorganic fillers is not subject to any particular restrictions here, and all known inorganic, particulate, dental fillers can be used, in particular the above-named inorganic fillers. Polymers filled with inorganic fillers are called organic-inorganic composite fillers. The above-defined monomers and fillers are suitable for the preparation of the ground prepolymers and pearl polymers. Compositions for the production of complete dentures preferably contain exclusively organic fillers, particularly preferably ground polymers or pearl polymers based on polymethyl methacrylate (PMMA), quite particularly preferably pearl polymers based on PMMA, as fillers. Fillers which are obtained by grinding quartz, radiopaque glasses, borosilicates, ceramic or prepolymers usually consist of splintery parts.

Unless otherwise stated, all particle sizes are weight-average particle sizes, wherein the particle-size determination in the range of from 0.1 μm to 1000 μm is effected by means of static light scattering, preferably using an LA-960 static laser scattering particle size analyzer (Horiba, Japan). Here, a laser diode with a wavelength of 655 nm and an LED with a wavelength of 405 nm are used as light sources. The use of two light sources with different wavelengths makes it possible to measure the entire particle-size distribution of a sample in only one measurement pass, wherein the measurement is carried out as a wet measurement. For this, a 0.1 to 0.5% aqueous dispersion of the filler is prepared and the scattered light thereof is measured in a flow cell. The scattered-light analysis for calculating particle size and particle-size distribution is effected in accordance with the Mie theory according to DIN/ISO 13320.

Particle sizes smaller than 0.1 μm are preferably determined by means of dynamic light scattering (DLS). The measurement of the particle size in the range of from 5 nm to 0.1 μm is preferably effected by dynamic light scattering (DLS) of aqueous particle dispersions, preferably with a Malvern Zetasizer Nano ZS (Malvern Instruments, Malvern UK) with an He—Ne laser with a wavelength of 633 nm, at a scattering angle of 90° at 25° C.

Particle sizes smaller than 0.1 μm can also be determined by means of SEM or TEM spectroscopy. The transmission electron microscopy (TEM) is preferably carried out using a Philips CM30 TEM at an accelerating voltage of 300 kV. For the preparation of the samples, drops of the particle dispersion are applied to a 50 Å thick copper grid (mesh size 300), which is coated with carbon, and then the solvent is evaporated.

The light scattering decreases as the particle size decreases, but fillers with a small particle size have a greater thickening action. The fillers are divided according to their particle size into macrofillers and microfillers, wherein fillers with an average particle size of from 0.2 to 10 μm are called macrofillers and fillers with an average particle size of from approximately 5 to 100 nm are called microfillers. Macrofillers are obtained e.g., by grinding e.g., quartz, radiopaque glasses, borosilicates or ceramic and usually consist of splintery parts. Microfillers such as mixed oxides can be prepared e.g., by hydrolytic co-condensation of metal alkoxides.

To improve the bond between the filler particles and the crosslinked polymerization matrix, the fillers are preferably surface-modified, particularly preferably by silanization, quite particularly preferably by radically polymerizable silanes, in particular with 3-methacryloyloxypropyltrimethoxysilane. For the surface modification of non-silicate fillers, e.g., of $ZrO_2$ or $TiO_2$, functionalized acidic phosphates, such as e.g., 10-methacryloyloxydecyl dihydrogen phosphate, can also be used.

Moreover, the compositions according to the invention can contain one or more further additives, above all stabilizers, colorants, microbiocidal active ingredients, fluoride-ion-releasing additives, foaming agents, optical brighteners, plasticizers and/or UV absorbers.

The compositions according to the invention are particularly suitable as dental materials, in particular as dental cements, filling composites and veneering materials as well as materials for the production of prostheses, artificial teeth, inlays, onlays, crowns and bridges. The compositions are suitable primarily for intraoral application by the dentist for the treatment of damaged teeth, i.e., for therapeutic application, e.g., as dental cements, filling composites and veneering materials. However, they can also be used non-therapeutically (extraorally), for example in the production or repair of dental restorations, such as prostheses, artificial teeth, inlays, onlays, crowns and bridges.

The compositions according to the invention are moreover suitable as materials for the production of shaped bodies for dental, but also for non-dental purposes, which can be produced e.g., by means of casting, compression moulding and in particular by additive processes such as 3D printing or stereolithography.

Compositions which Contain:
(a) 0.5 to 15 wt.-%, preferably 1.0 to 12.0 wt.-%, of at least one CHP oligomer of Formula I,
(b) 0.01 to 5 wt.-%, preferably 0.05 to 2.0 wt.-%, of at least one accelerator,
(c) 5 to 95 wt.-%, preferably 10 to 95 wt.-%, of at least one radically polymerizable monomer,
(d) 0 to 80 wt.-%, preferably 10 to 80 wt.-%, filler(s) and
(e) 0.001 to 5 wt.-%, preferably 0.01 to 3 wt.-%, additive(s).

are preferred according to the invention for the use as dental material.

All quantities herein are relative to the total mass of the composition, unless otherwise stated.

Compositions for Use as Dental Cements or Filling Composites Preferably Contain:
(a) 0.5 to 10 wt.-%, preferably 1.0 to 8.0 wt.-% and particularly preferably 1.5 to 5.0 wt.-%, of at least one CHP oligomer of Formula I,
(b) 0.01 to 5 wt.-%, preferably 0.02 to 3.0 wt.-% and particularly preferably 0.05 to 2.0 wt.-%, of at least one accelerator,
(c) 5 to 95 wt.-%, preferably 10 to 95 wt.-% and particularly preferably 10 to 90 wt.-%, of at least one radically polymerizable monomer,
(d) 0 to 80 wt.-% filler(s) and
(e) 0.001 to 5 wt.-%, preferably 0.01 to 3 wt.-% and particularly preferably 0.015 to 2 wt.-% additive(s).

The filling level is geared towards the desired intended use of the composition. Filling composites preferably have a filler content of from 50 to 80 wt.-% and dental cements of from 10 to 70 wt.-%.

Compositions for the Production of Complete Dentures Preferably Contain:
(a) 0.5 to 15 wt.-%, preferably 1.0 to 12.0 wt.-% and particularly preferably 2.0 to 10.0 wt.-%, of at least one CHP oligomer of Formula I,
(b) 0.01 to 5 wt.-%, preferably 0.02 to 3.0 wt.-% and particularly preferably 0.05 to 2.0 wt.-%, of at least one accelerator,
(c) 20 to 95 wt.-%, preferably 30 to 95 wt.-% and particularly preferably 35 to 95 wt.-%, of at least one radically polymerizable monomer,
(d) 5 to 80 wt.-%, preferably 10 to 70 wt.-% and particularly preferably 20 to 60 wt.-%, pearl polymer(s) and
(e) 0.001 to 5 wt.-%, preferably 0.01 to 3 wt.-% and particularly preferably 0.015 to 2 wt.-%, additive(s).

In all cases, compositions which additionally contain
(f) 0.0001 to 1 wt.-%, preferably 0.0005 to 0.5 wt.-%, particularly preferably 0.0007 to 0.02 wt.-%, of at least one transition metal compound are particularly preferred.

Materials which comprise two physically separated components which are mixed with each other for use are preferred according to the invention. The first component (catalyst paste) contains the CHP oligomer or oligomers of Formula I, and the second component (base paste) contains the accelerator or accelerators, preferably one or more thiourea derivatives, and, where applicable, the transition metal compound. Base paste and catalyst paste are preferably mixed with each other in a volume ratio of 1:1. The curing reaction is initiated by mixing base and catalyst pastes. The compositions specified above relate to the mixed pastes.

Those compositions which consist of the named constituents are particularly preferred for use as dental materials, wherein the individual constituents are preferably in each case selected from the above-named preferred and particularly preferred substances. In all cases, a mixture of several substances, thus for example a mixture of monomers, can also be used as respective constituent.

The invention is explained in more detail in the following with reference to embodiment examples.

EMBODIMENT EXAMPLES

Example 1

Synthesis of 4-isopropylbenzoic acid-(2-methacryloyloxyethyl) ester (IPBMEE)

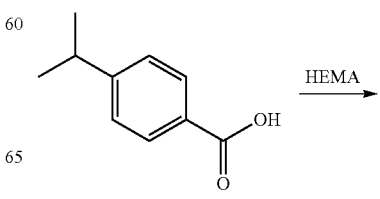

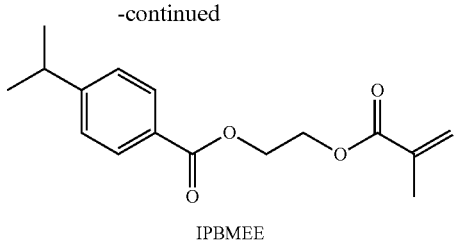

IPBMEE 76.68 g (0.40 mol) N-(3-dimethylaminopropyl)-N'-ethylcarbodiimide hydrochloride was added in portions at 0–5° C. to a solution of 52.06 g (0.40 mol) 2-hydroxyethyl methacrylate (HEMA), 59.11 g (0.36 mol) 4-isopropylbenzoic acid and 2.20 g (0.018 mol) 4-dimethylaminopyridine in 250 ml methylene chloride. The yellow solution was stirred in a melting ice bath for 5 h and then subjected to aqueous work-up (3×200 ml 1 N hydrochloric acid, 3×200 ml 1 N sodium hydroxide solution, 4×200 ml deionized water, 2×100 ml saturated sodium chloride solution). The organic phase was dried with anhydrous magnesium sulfate, filtered and released from the solvent after the addition of 25 mg BHT with the introduction of a light air flow. The obtained residue (78.9 g) was chromatographed over silica gel 60 (0.03–0.2 mm) with n-heptane/ethyl acetate (5:1) as eluent. 49.7 g (50% yield) IPBMEE was obtained as a clear, colourless liquid with a purity of 99.66% (HPLC).

$^{1}$H-NMR (CDCl$_3$, 400 MHz): δ (ppm)=1.26 [d, J=7 Hz, 6H, HC(C$\underline{H}_3$)$_2$], 1.95 (s, 3H, CH$_3$), 2.96 (sept, J=7 Hz, 1H, $\underline{H}$C(CH$_3$)$_2$], 4.47–4.50 and 4.54–4.57 (2 m, each 2H, OCH$_2$), 5.58 and 6.14 (2 s, each 1H, =CH$_2$), 7.29 and 7.97 (2 d, each J=8 Hz, each 2H, =CH). $^{13}$C-NMR (CDCl$_3$, 100 MHz): δ(ppm)=18.3 (CH$_3$), 23.7 [HC ($\underline{C}$H$_3$)$_2$], 34.3 [$\underline{H}$C (CH$_3$)$_2$], 66.4 and 66.5 (OCH$_2$), 126.0 ($\underline{C}$=CH$_2$), 126.5 and 129.9 (=CH), 127.5 and 154.6 (=C), 136.0 ($\underline{C}$=CH$_2$), 166.3 and 167.1 (C=O).

Example 2

Synthesis of 2-{[2-(4-isopropylphenoxy)ethoxycarbonyl]amino}ethyl methacrylate (IPPECEM)

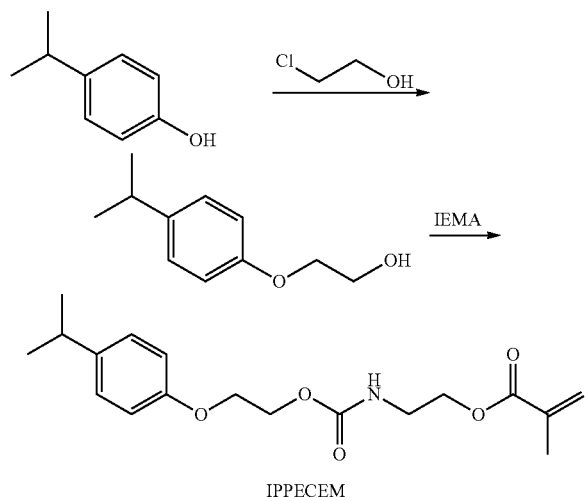

IPPECEM

1$^{st}$ stage: 4-(isopropylphenoxy)-ethanol (IPPE)

75.6 g (555 mmol) 4-isopropylphenol was dissolved in sodium hydroxide solution (33.2 g (830 mmol) sodium hydroxide in 0.5 l water). After the addition of 8.85 g (27.5 mmol) benzyltributylammonium chloride and 4.56 g (27.5 mmol) potassium iodide, 66.8 g (830 mmol) 2-chloroethanol was added dropwise at 40° C. The cloudy reaction mixture was stirred for 18 h at 60° C. After the mixture had cooled, 250 ml toluene was added, it was stirred for 15 min and then the phases were left to separate. The aqueous phase was extracted a further 2× with 250 ml toluene each time. The combined toluene phases were washed successively with 4×100 ml of each of 1 N sodium hydroxide solution, 1 N hydrochloric acid and water. After the organic phase had been dried with anhydrous sodium sulfate, the toluene was removed in vacuo.

The distillation of the crude product (Kp=$^{9}$5–$^{97°}$C$_{\cdot 0.1\ mbar}$) provided 84.4 g (84% yield) 4-(isopropylphenoxy)-ethanol IPPE as a pale-yellow oil with a purity of 100% (HPLC).

$^{1}$H-NMR (400 MHz, CDCl$_3$): δ (ppm)=1.21 [d, J=7 Hz, 6H, HC(C$\underline{H}_3$)$_2$], 2.73 (t, J=6 Hz, 1H, OH), 2.85 [sept, J=7 Hz, $\underline{H}$C(CH$_3$)$_2$], 3.89–3.92 (m, 2H, C$\underline{H}_2$OH), 4.02 (t, J=5 Hz, 2H, OCH$_2$), 6.83 and 7.12 (2 d, each J=9 Hz, each 2H, =CH).

$^{13}$C-NMR (100 MHz, CDCl$_3$): δ (ppm)=24.3 [HC ($\underline{C}$H$_3$)$_2$], 33.3 [H$\underline{C}$(CH$_3$)$_2$], 61.5 and 69.3 (OCH$_2$), 114.5 (=CH$_{2,6}$), 127.4 (=CH$_{3,5}$), 141.6 (=C$_4$), 156.7 (=C$_1$).

2$^{nd}$ stage: 2-{[2-(4-isopropylphenoxy)-ethoxycarbonyl]-amino}-ethyl methacrylate (IPPECEM)

40 mg Metatin 712 (dibutyltin dilaurate, CAS 77–58–7) and 16 mg BHT were dissolved in 30.0 g (166 mmol) 4-(isopropyl-phenoxy)-ethanol IPPE. The dropwise addition of 28.8 g (166 mmol) 2-isocyanatoethyl methacrylate (IEMA) was begun at an internal temperature of 40° C. In the process, the internal temperature increased rapidly; 80° C. was not exceeded. After the addition of the isocyanate had ended, the reaction mixture was stirred for a further 15 min at a bath temperature of 50° C. and the course of the reaction was tracked by IR spectroscopy. Once no more isocyanate radicals were detected, 0.5 ml anhydrous ethanol was added and the mixture was cooled to room temperature after 1 h. The mixture was diluted with 100 ml methylene chloride and washed as follows: 2× with 50 ml 1 N sodium hydroxide solution each time, 1× with 50 ml 1 N hydrochloric acid and 2× with 50 ml water each time. The organic phase was dried with anhydrous sodium sulfate and the solvent was distilled off in vacuo. 54.6 g (98% yield) 2-{[2-(4-isopropylphenoxy)-ethoxycarbonyl]-amino}-ethyl methacrylate (IPPECEM) was obtained as a colourless oil with a purity of 99.51% (HPLC).

$^{1}$H-NMR (400 MHz, CDCl$_3$): δ (ppm)=1.21 [d, J=7 Hz, 6H, HC(C$\underline{H}_3$)$_2$], 1.93 (s, 3H, CH$_3$), 2.85 [sept, J=7 Hz, $\underline{H}$C(CH$_3$)$_2$], 3.50 (q, J=5.5 Hz, 2H, NCH$_2$), 4.12 and 4.41 (2 q, each J=5 Hz, each 2H, OC$\underline{H}_2$C$\underline{H}_2$O), 4.22 (q, J=5 Hz, 2H, NCH$_2$C$\underline{H}_2$O), 5.16 (br s, 1H NH), 5.75 and 6.11 (2 s, each 1H, =C$\underline{H}_2$), 6.83 and 7.13 (2 d, J=9 Hz, each 2H, =CH).

$^{13}$C-NMR (100 MHz, CDCl$_3$): δ (ppm)=18.3 (CH$_3$), 24.2 [HC($\underline{C}$H$_3$)$_2$], 33.3 [H$\underline{C}$(CH$_3$)$_2$], 40.2 (NCH$_2$), 63.5, 63.6 and 66.4 (OCH$_2$), 114.4 (=CH$_{2,6}$), 126.0 ($\underline{C}$=CH$_2$), 127.3 (=CH$_{3,5}$), 135.9 ($\underline{C}$=CH$_2$), 141.6 (=C$_4$), 156.2 (=C$_1$, C=O$_{urethane}$), 167.2 (C=O$_{methacrylic}$).

Example 3

Synthesis of a CHP oligomer of Formula I: poly[methyl methacrylate-co-{4-isopropylbenzoic acid-(2-methacryloyloxyethyl)-ester}] 1:1 (x/y=1), with sulfone end group (PCHP-1, $M_n$: 2600 g/mol)

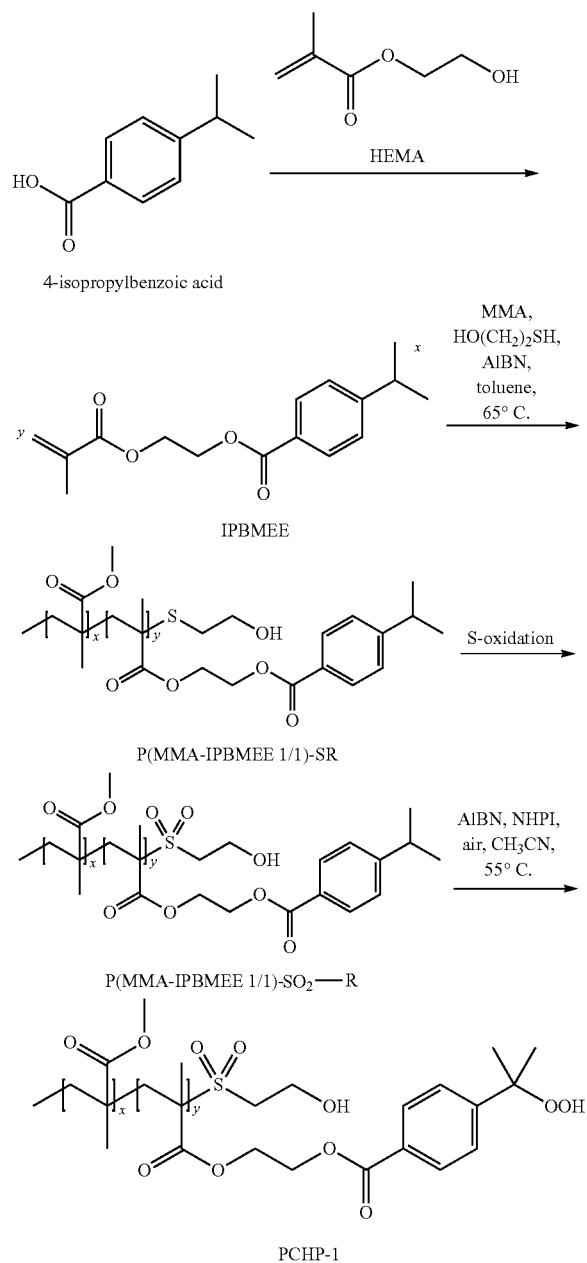

1$^{st}$ stage: synthesis of poly(MMA-co-IPBMEE) 1:1 with thioether end group (P(MMA-IPBMEE 1/1)—SR)

3.72 g (13.46 mmol) IPBMEE, 1.348 g (13.46 mmol) methyl methacrylate (MMA), 0.044 g (0.268 mmol) azobisisobutyronitrile (AIBN) and 0.237 g (3.03 mmol) 2-mercaptoethanol were dissolved in 5 ml toluene. Then, a stream of nitrogen gas was passed through the solution at 0° C. and the solution was stirred at 65° C. in an $N_2$ atmosphere. After 16 h, the solution was cooled to room temperature and slowly added dropwise to 500 ml methanol at 0° C. with stirring. The precipitated polymer solid was filtered off and dried to constant weight at 60° C. in a fine vacuum. 3.5 g (70% yield) of P(MMA-IPBMEE 1/1)—SR was obtained as a white powder.

$^1$H-NMR (CDCl$_3$, 400 MHz): δ (ppm)=0.7–1.2 [CH$_3$CCO], 1.2–1.3 [(CH$_3$)$_2$CH], 1.5–2.1 [CH$_2$C], 2.4–2.7 [CH$_2$S], 2.9–3.0 [HC(CH$_3$)$_2$], 3.4–3.7 [OCH$_3$ and CH$_2$OH], 4.1–4.6 [CH$_2$OCOAr, CH$_2$OCOC], 7.2–8.1 [CH$_{Ar}$].

2$^{nd}$ stage: synthesis of poly(MMA-co-IPBMEE) 1:1 with sulfone end group (P(MMA-IPBMEE 1/1)—SO$_2$—R)

3 g of P(MMA-IPBMEE 1/1)—SR, which contained 1.2 mmol thioether groups, was dissolved in 20 ml methylene chloride and the solution was cooled to −5° C. After the addition of 10 ml ethanol and 0.831 g (1.68 mmol) magnesium monoperoxyphthalate hexahydrate, the reaction mixture was stirred for 18 h at room temperature. Then, the solvent was removed in vacuo and the white solid left behind was dissolved in 3 ml toluene. This solution was then slowly added dropwise to 300 ml methanol at 0° C. The precipitated polymer solid was filtered off and dried to constant weight at 60° C. in a fine vacuum. 2.35 g (78% yield) of P(MMA-IPBMEE 1/1)—SO$_2$—R was obtained as a white solid.

$^1$H-NMR (CDCl$_3$, 400 MHz): δ (ppm)=0.7–1.2 [CH$_3$CCO], 1.2–1.3 [(CH$_3$)$_2$CH], 1.5–2.1 [CH$_2$C], 2.9–3.0 [HC(CH$_3$)$_2$], 3.0–3.2 [CH$_2$SO$_2$], 3.4–3.7 [OCH$_3$], 3.9–4.1 [CH$_2$OH], 4.1–4.6 [CH$_2$OCOAr, CH$_2$OCOC], 7.2–8.1 [CH$_{Ar}$].

3$^{rd}$ stage: peroxidation of P(MMA-IPBMEE 1/1)—SO$_2$—R) to form PCHP-1

2.35 g (contain 6.04 mmol isopropyl groups) of P(MMA-IPBMEE 1/1)—SO$_2$—R, 0.049 g (0.3 mmol) N-hydroxyphthalimide and 0.06 g (0.365 mmol) AIBN were dissolved in 25 ml acetonitrile. The solution was heated to 55° C. and a light air flow was passed through it. 0.06 g (0.365 mmol) AIBN was added every 24 h. After 96 h reaction time, the reaction was tracked by means of $^1$H-NMR spectroscopy, the solution was cooled to room temperature and slowly added dropwise to 500 ml cold water (4° C.). After the solution had been filtered, the solid formed was dissolved in 25 ml acetonitrile. This solution was then again added dropwise to 500 ml cold water and thus the polymer precipitated out again. The reprecipitation was repeated once more. The colourless solid was dried in a freeze dryer. 1.94 g (83% yield) of PCHP-1 was obtained as a white powder. 88% of the isopropyl groups had been successfully converted into the corresponding hydroperoxide groups. A number-average molar mass $M_n$ of 2600 g/mol was determined in tetrahydrofuran (THF) by means of gel permeation chromatography (GPC), wherein n~ 5.

The GPC analyses were carried out by means of a Varian 390-LC GPC device with a refractive index detector equipped with 2 5 μm PLGel columns using THF+0.05 wt.-% toluene as eluent at 30° C. and a flow rate of 1 ml/min. Linear PMMA was used as standard.

$^1$H-NMR (CDCl$_3$, 400 MHz): δ (ppm)=0.7–1.2 [CH$_3$CCO], 1.2–1.3 [(CH$_3$)$_2$CH radicals], 1.5–1.7 [(CH$_3$)$_2$C], 1.5–2.1 [CH$_2$C], 2.9–3.0 [HC(CH$_3$)$_2$ radicals], 3.0–3.2 [CH$_2$SO$_2$], 3.4–3.7 [OCH$_3$], 3.9–4.1 [CH$_2$OH], 4.1–4.6 [CH$_2$OCOAr, CH$_2$OCOC], 7.4–8.1 [CH$_{Ar}$].

Example 4

Synthesis of a CHP oligomer of Formula I: poly{methyl methacrylate-co-[4-isopropylbenzoic acid-(2-methacryloyloxyethyl)-ester]}1:3 (x/y=0.33), with sulfone end group (PCHP-2, $M_n$: 2400 g/mol)

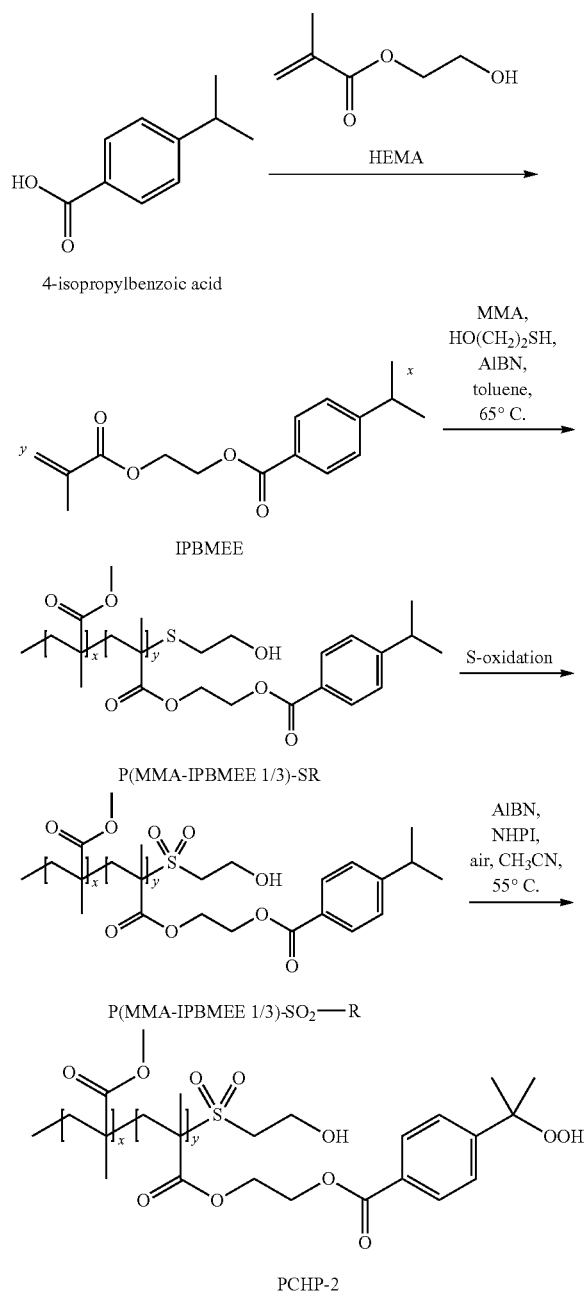

1$^{st}$ stage: synthesis of poly(MMA-co-IPBMEE) 1:3 with thioether end group (P(MMA-IPBMEE 1/3)—SR)

5.353 g (19.37 mmol) IPBMEE, 0.647 g (6.46 mmol) MMA, 0.041 g (0.254 mmol) AIBN and 0.280 g (3.59 mmol) 2-mercaptoethanol were dissolved in 6 ml toluene. After a stream of $N_2$ gas had been passed through at 0° C., the solution was stirred at 65° C. in an $N_2$ atmosphere. After 16 h, the reaction solution was cooled to room temperature and added dropwise to 600 ml methanol at 0° C. with stirring. After the solution had been filtered, the solid formed was filtered off and dried to constant weight in a fine vacuum. 4.8 g (80% yield) of P(MMA-IPBMEE 1/3)—SR was obtained as a white powder.

$^1$H-NMR (CDCl$_3$, 400 MHz): δ (ppm)=0.7–1.2 [CH$_3$CCO], 1.2–1.3 [(CH$_3$)$_2$CH], 1.5–2.1 [CH$_2$C], 2.4–2.7 [CH$_2$S], 2.9–3.0 [HC(CH$_3$)$_2$], 3.4–3.7 [OCH$_3$ and CH$_2$OH], 4.1–4.6 [CH$_2$OCOAr, CH$_2$OCOC], 7.2–8.1 [CH$_{Ar}$].

2$^{nd}$ stage: synthesis of poly(MMA-co-IPBMEE) 1:3 with sulfone end group (P(MMA-IPBMEE 1/3)—SO$_2$—R)

3.8 g of P(MMA-IPBMEE 1/3)—SR, which contained 1.58 mmol thioether groups, was dissolved in 25 ml methylene chloride. After the solution had been cooled to −5° C., 13 ml ethanol and 1.096 g (2.22 mmol) magnesium monoperoxyphthalate hexahydrate were added and the reaction solution was stirred for 18 h at room temperature. For work-up, the solvent was removed in vacuo and the white solid was dissolved in 3.8 ml toluene. The solution obtained was finally added dropwise to 400 ml methanol at 0° C. The precipitated polymer solid was filtered off and dried to constant weight at 60° C. in a fine vacuum. 2.94 g (77% yield) of P(MMA-IPBMEE 1/3)—SO$_2$—R was obtained as a white solid.

$^1$H-NMR (CDCl$_3$, 400 MHz): δ (ppm)=0.7–1.2 [CH$_3$CCO], 1.2–1.3 [(CH$_3$)$_2$CH], 1.5–2.1 [CH$_2$C], 2.9–3.0 [HC(CH$_3$)$_2$], 3.0–3.2 [CH$_2$SO$_2$], 3.4–3.7 [OCH$_3$], 3.9–4.1 [CH$_2$OH], 4.1–4.6 [CH$_2$OCOAr, CH$_2$OCOC], 7.2–8.1 [CH$_{Ar}$].

3$^{rd}$ stage: peroxidation of P(MMA-IPBMEE 1/3)—SO$_2$—R) to form PCHP-2

2.7 g (contain 8.44 mmol isopropyl groups) of P(MMA-IPBMEE 1/3)—SO$_2$—R, 0.069 g (0.42 mmol) N-hydroxyphthalimide and 0.083 g (0.51 mmol) AIBN were dissolved in 27 ml acetonitrile. The resulting solution was heated to 55° C. and a light air flow was passed through the solution. 0.083 g (0.51 mmol) AIBN was added every 24 h. After 96 h reaction time, the reaction was tracked by means of $^1$H-NMR spectroscopy, the solution was cooled to room temperature and slowly added dropwise to 500 ml cold water (4° C.). After the solution had been filtered, the solid formed was dissolved in 27 ml acetonitrile. This solution was then added dropwise to 500 ml cold water and thus the polymer precipitated out again. The reprecipitation was repeated once more. The colourless solid formed was dried in a freeze dryer. 2.59 g (96% yield) of PCHP-2 was obtained as a white powder. 85% of the isopropyl groups had been successfully converted into the corresponding hydroperoxide groups. A number-average molar mass $M_n$ of 2400 g/mol was determined in THF by means of GPC, wherein n~6.

$^1$H-NMR (CDCl$_3$, 400 MHz): δ (ppm)=0.7–1.2 [CH$_3$CCO], 1.2–1.3 [(CH$_3$)$_2$CH radicals], 1.5–1.7 [(CH$_3$)$_2$C], 1.5–2.1 [CH$_2$C], 2.9–3.0 [HC(CH$_3$)$_2$ radicals], 3.0–3.2 [CH$_2$SO$_2$], 3.4–3.7 [OCH$_3$]3.9–4.1 [CH$_2$OH], 4.1–4.6 [CH$_2$OCOAr, CH$_2$OCOC], 7.4–8.1 [CH$_{Ar}$].

Example 5

Synthesis of a CHP oligomer of Formula I: poly{methyl methacrylate-co-[4-isopropylbenzoic acid-(2-methacryloyloxyethyl)-ester]} 1:3 (x/y=0.33), with sulfone end group (PCHP-3, $M_n$: 5000 g/mol)

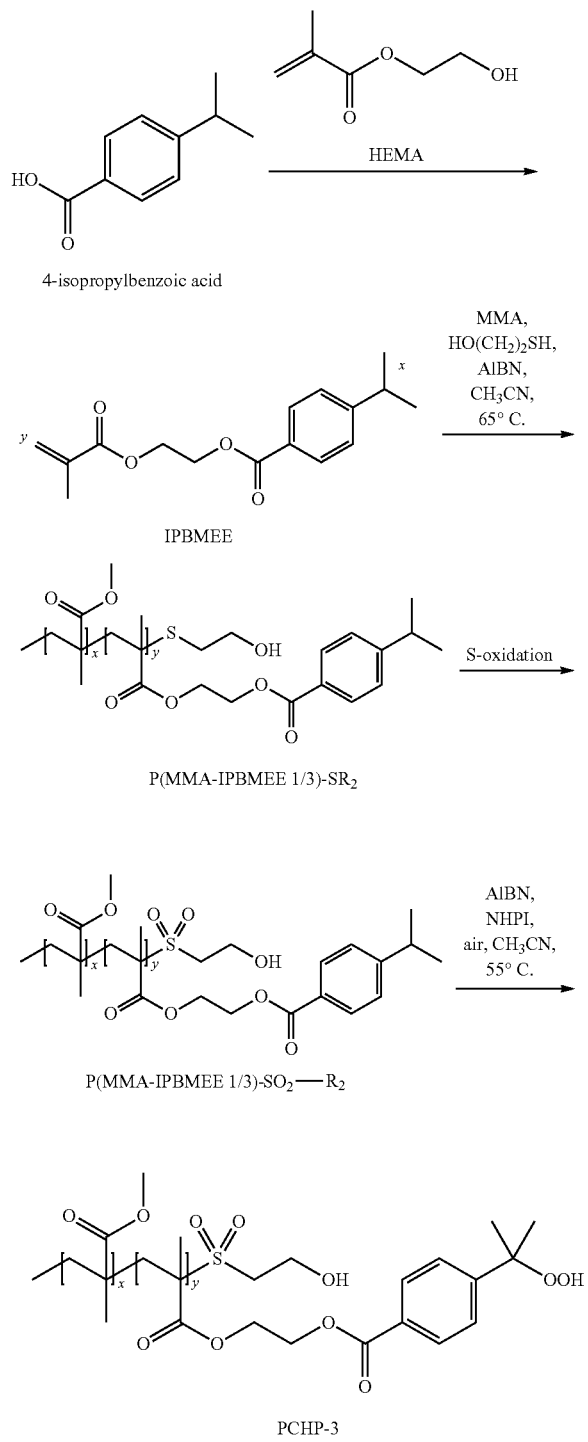

1$^{st}$ stage: synthesis of poly(MMA-co-IPBMEE) 1:3 with thioether end group (P(MMA-IPBMEE 1/3)—SR)

4.461 g (16.15 mmol) IPBMEE, 0.539 g (5.38 mmol) MMA, 0.035 g (0.22 mmol) AIBN and 0.115 g (1.47 mmol) 2-mercaptoethanol were dissolved in 5 ml toluene. After a stream of $N_2$ gas had been passed through at 0° C., the solution was stirred at 65° C. in an $N_2$ atmosphere. After 16 h, the reaction solution was cooled to room temperature and added dropwise to 500 ml methanol at 0° C. with stirring. After the solution had been filtered, the solid formed was filtered off and dried to constant weight in a fine vacuum. 4.0 g (80% yield) of P(MMA-IPBMEE 1/3)—SR was obtained as a white powder.

$^1$H-NMR (CDCl$_3$, 400 MHz): δ (ppm)=0.7–1.2 [CH$_3$CCO], 1.2–1.3 [(CH$_3$)$_2$CH], 1.5–2.1 [CH$_2$C], 2.4–2.7 [CH$_2$S], 2.9–3.0 [HC(CH$_3$)$_2$], 3.4–3.7 [OCH$_3$ and CH$_2$OH], 4.1–4.6 [CH$_2$OCOAr, CH$_2$OCOC], 7.2–8.1 [CH$_{Ar}$].

2$^{nd}$ stage: synthesis of poly(MMA-co-IPBMEE) 1:3 with sulfone end group (P(MMA-IPBMEE 1/3)—SO$_2$—R)

3.0 g (contain 0.6 mmol thioether groups) of P(MMA-IPBMEE 1/3)—SR was dissolved in 20 ml methylene chloride and the solution was cooled to −5° C. 10 ml ethanol and 0.415 g (0.94 mmol) magnesium monoperoxyphthalate hexahydrate were added and the reaction mixture was stirred for 18 h at room temperature. Then, the solvent was separated off in a fine vacuum and the white solid was dissolved in 3.0 ml toluene.

The solution was slowly added dropwise to 300 ml methanol at 0° C. The precipitated polymer solid was filtered off and dried to constant weight at 60° C. in a fine vacuum. 2.40 g (80% yield) of P(MMA-IPBMEE 1/3)—SO$_2$—R was obtained as a white solid.

$^1$H-NMR (CDCl$_3$, 400 MHz): δ (ppm)=0.7–1.2 [CH$_3$CCO], 1.2–1.3 [(CH$_3$)$_2$CH], 1.5–2.1 [CH$_2$C], 2.9–3.0 [HC(CH$_3$)$_2$], 3.0–3.2 [CH$_2$SO$_2$], 3.4–3.7 [OCH$_3$] 3.9–4.1 [CH$_2$OH], 4.1–4.6 [CH$_2$OCOAr, CH$_2$OCOC], 7.2–8.1 [CH$_{Ar}$].

3$^{rd}$ stage: peroxidation of P(MMA-IPBMEE 1/3)—SO$_2$—R to form PCHP-3

2.0 g (contain 6.33 mmol isopropyl groups) of P(MMA-IPBMEE 1/3)—SO$_2$—R, 0.052 g (0.32 mmol) N-hydroxyphthalimide and 0.062 g (0.38 mmol) AIBN were dissolved in 20 ml acetonitrile. The resulting solution was heated to 55° C. and a light air flow was passed through the solution. 0.062 g (0.38 mmol) AIBN was added every 24 h. After 96 h reaction time, the reaction was tracked by means of $^1$H-NMR spectroscopy, the solution was cooled to room temperature and slowly added dropwise to 400 ml cold water (4° C.). After the solution had been filtered, the solid formed was dissolved in 20 ml acetonitrile. This solution was then again added dropwise to 400 ml cold water and thus the polymer precipitated out again. The reprecipitation was repeated once more. The colourless solid formed was dried in a freeze dryer. 1.5 g (75% yield) of PCHP-3 was obtained as a white powder. 84% of the isopropyl groups had been successfully converted into the corresponding hydroperoxide groups. A number-average molar mass $M_n$ of 4900 g/mol was determined in THF by means of GPC, wherein n~12.

$^1$H-NMR (CDCl$_3$, 400 MHz): δ (ppm)=0.7–1.2 [CH$_3$CCO], 1.2–1.3 [(CH$_3$)$_2$CH radicals], 1.5–1.7 [(CH$_3$)$_2$C], 1.5–2.1 [CH$_2$C], 2.9–3.0 [HC(CH$_3$)$_2$ $_{radicals}$], 3.0–3.2 [CH$_2$SO$_2$], 3.4–3.7 [OCH$_3$], 3.9–4.1 [CH$_2$OH], 4.1–4.6 [CH$_2$OCOAr, CH$_2$OCOC], 7.4–8.1 [CH$_{Ar}$].

Example 6

Synthesis of a CHP oligomer of Formula I: poly{4-isopropylbenzoic acid-(2-methacryloyloxyethyl)-ester]} with sulfone end group (PCHP-4, $M_n$: 2800 g/mol)

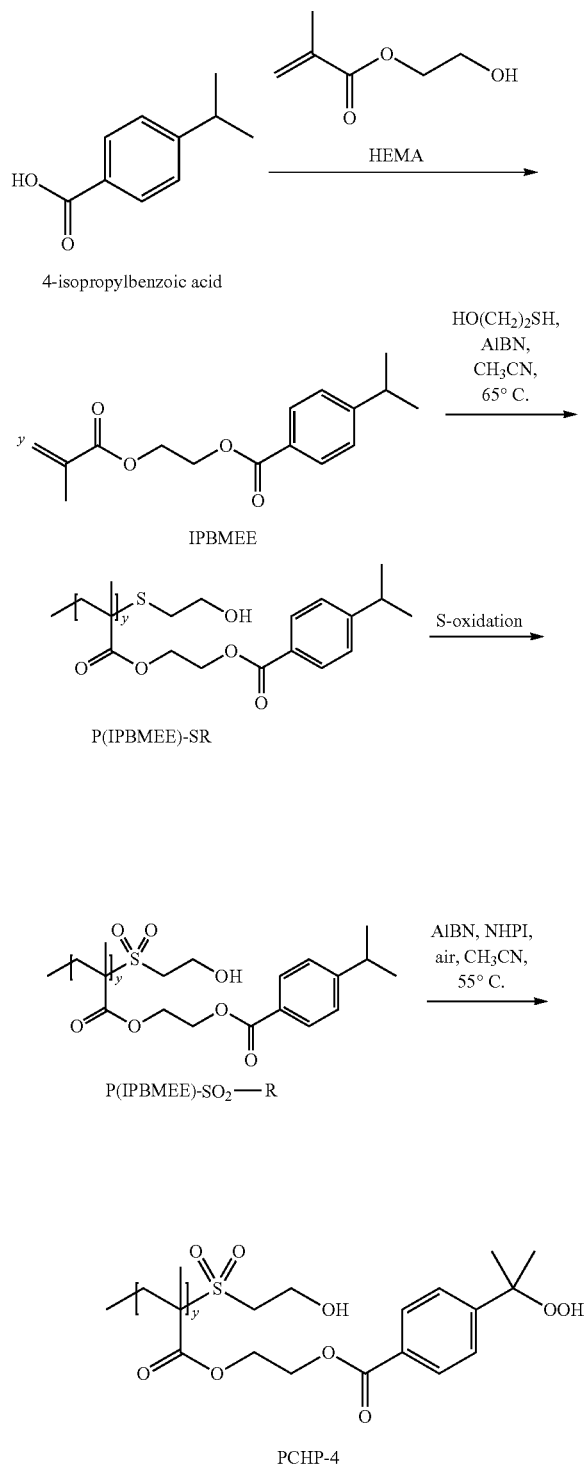

1st stage: synthesis of poly(IPBMEE) with thioether end group end group (PIPBMEE)-SR)

6.0 g (21.71 mmol) IPBMEE, 0.036 g (0.217 mmol) AIBN and 0.281 g (3.59 mmol) 2-mercaptoethanol were dissolved in 6 ml toluene. After a stream of $N_2$ gas had been passed through at 0° C., the solution was stirred at 65° C. in a $N_2$ atmosphere. After 16 h, the reaction solution was cooled to room temperature and added dropwise to 600 ml methanol at 0° C. with stirring. After the solution had been filtered, the solid formed was filtered off and dried to constant weight at 60° C. in a fine vacuum. 3.92 g (65% yield) of P(IPBMEE)-SR was obtained as a white powder.

$^1$H-NMR (CDCl$_3$, 400 MHz): δ (ppm)=0.7–1.2 [CH$_3$CCO], 1.2–1.3 [(C$\underline{H}_3$)$_2$CH], 1.5–2.1 [CH$_2$C], 2.4–2.7 [CH$_2$S], 2.9–3.0 [$\underline{H}$C(CH$_3$)$_2$], 3.5–3.6 [CH$_2$OH], 4.1–4.6 [CH$_2$OCOAr, CH$_2$OCOC], 7.2–8.1 [CH$_{Ar}$].

2$^d$ stage: synthesis of poly(IPBMEE) sulfone end group (P(IPBMEE)-SO$_2$—R)

3.2 g (contain 1.143 mmol thioether groups) of P(IPBMEE)-SR was dissolved in 20 ml methylene chloride and the solution was cooled to -5° C. 10 ml ethanol and 0.791 g (1.60 mmol) magnesium monoperoxyphthalate hexahydrate were added and the reaction mixture was stirred for 18 h at room temperature. Then, the solvent was separated off in a fine vacuum and the white solid was dissolved in 3.2 ml toluene. The solution was slowly added dropwise to 300 ml methanol at 0° C. The precipitated polymer solid was filtered off and dried to constant weight at 60° C. in a fine vacuum. 2.74 g (86% yield) of P(IPBMEE)-SO$_2$—R was obtained as a white solid.

$^1$H-NMR (CDCl$_3$, 400 MHz): δ (ppm)=0.7–1.2 [CH$_3$CCO], 1.2–1.3 [(C$\underline{H}_3$)$_2$CH], 1.5–2.1 [CH$_2$C], 2.8–3.0 [$\underline{H}$C(CH$_3$)$_2$], 3.0–3.2 [C$\underline{H}_2$SO$_2$], 3.9–4.0 [C$\underline{H}_2$OH], 4.1–4.6 [CH$_2$OCOAr, CH$_2$OCOC], 7.2–8.1 [CH$_{Ar}$].

3$^{rd}$ stage: peroxidation of P(IPBMEE)-SO$_2$—R with formation of PCHP-4

2.5 g (contain 8.79 mmol isopropyl groups) of P(IPBMEE)-SO$_2$—R, 0.072 g (0.44 mmol) N-hydroxyphthalimide and 0.087 g (0.53 mmol) AIBN were dissolved in 25 ml acetonitrile. The resulting solution was heated to 55° C. and a light air flow was passed through the solution. 0.087 g (0.53 mmol) AIBN was added every 24 h. After 96 h reaction time, the reaction was tracked by means of $^1$H-NMR spectroscopy, the solution was cooled to room temperature and slowly added dropwise to 500 ml cold water (4° C.). After the solution had been filtered, the solid formed was dissolved in 25 ml acetonitrile. This solution was then again added dropwise to 500 ml cold water and thus the polymer precipitated out again. The reprecipitation was repeated once more. The colourless solid formed was dried in a freeze dryer. 2.25 g (90% yield) of PCHP-4 was obtained as a white powder. 78% of the isopropyl groups had been successfully converted into the corresponding hydroperoxide groups. A number-average molar mass $M_n$ of 2800 g/mol was determined in THF by means of GPC, wherein n~7.

$^1$H-NMR (CDCl$_3$, 400 MHz): δ (ppm)=0.7–1.2 [CH$_3$CCO], 1.2–1.3 [(C$\underline{H}_3$)$_2$CH radicals], 1.5–1.7 [(CH$_3$)$_2$C], 1.5–2.1 [CH$_2$C], 2.9–3.0 [$\underline{H}$C(CH$_3$)$_2$ $_{radicals}$], 3.0–3.1 [C$\underline{H}_2$SO$_2$], 3.9–4.1 [C$\underline{H}_2$OH], 4.1–4.6 [CH$_2$OCOAr, CH$_2$OCOC], 7.4–8.1 [C$\underline{H}_{Ar}$].

Example 7

Synthesis of a CHP oligomer of Formula I: poly{methyl methacrylate-co-IPPECEM]}1:1 (x/y=1), with sulfone end group (PCHP-5, $M_n$: 6000 g/mol)

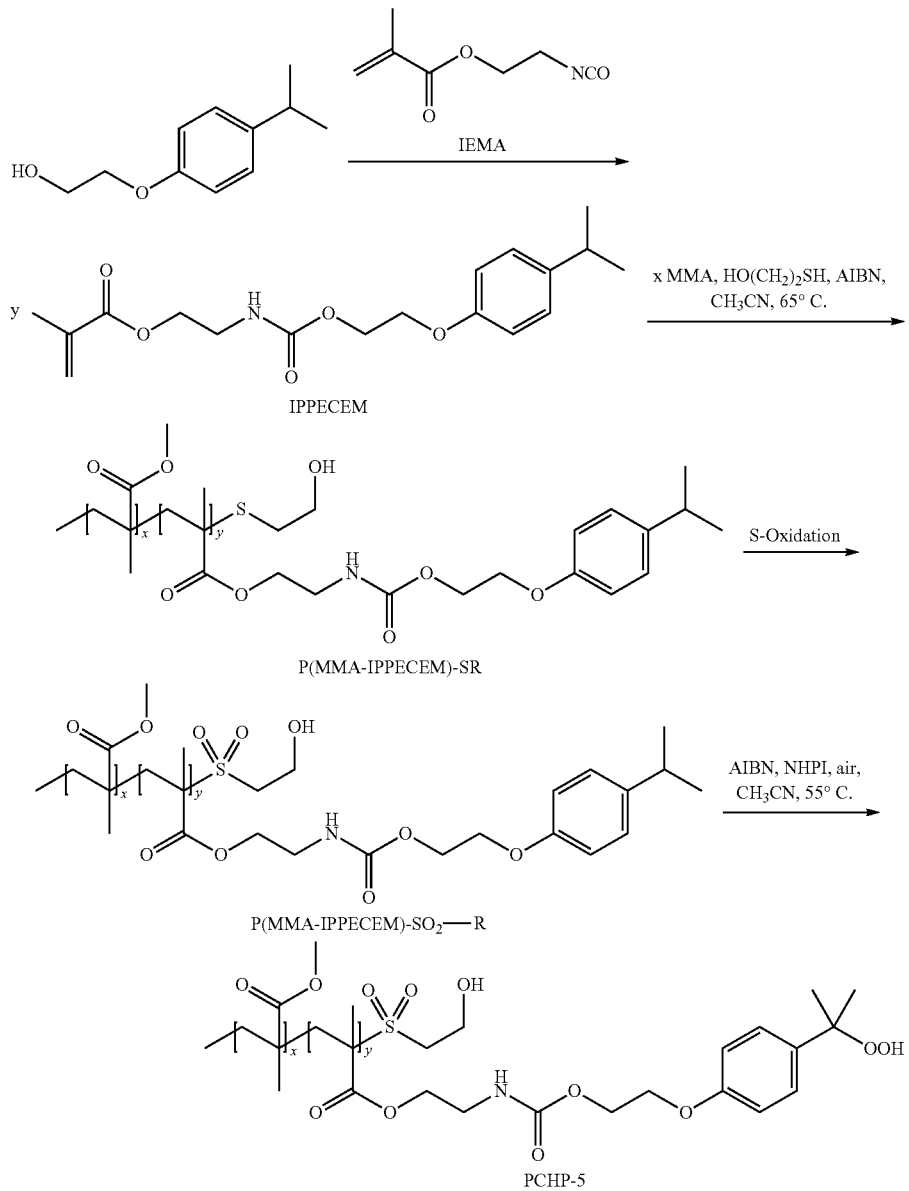

1st stage: synthesis of poly[methyl methacrylate-co-2-{[2-(4-isopropylphenoxy)ethoxycarbonyl]amino}ethyl methacrylate] 1:1 with thioether end group (P(MMA-IPPECEM)-SR)

3.85 g (11.48 mmol) IPPECEM, 1.149 g (11.48 mmol) MMA, 0.038 g (0.23 mmol) AIBN and 0.115 g (1.47 mmol) 2-mercaptoethanol were dissolved in 5 ml acetonitrile. After a stream of $N_2$ gas had been passed through at 0° C., the solution was stirred at 65° C. in an $N_2$ atmosphere. After 16 h, the reaction solution was cooled to room temperature and added dropwise to 500 ml methanol at 0° C. with stirring. After the solution had been filtered, the solid formed was filtered off and dried to constant weight at 60° C. in a fine vacuum. 3.63 g (73% yield) of P(MMA-IPPECEM)-SR was obtained as a white powder.

$^1$H-NMR (CDCl$_3$, 400 MHz): δ (ppm)=0.7–1.1 [CH$_3$CCO], 1.1–1.3 [(C$\underline{H}_3$)$_2$CH], 1.5–2.2 [CH$_2$C], 2.6–2.7 [br. CH$_2$S], 2.8–2.9 [$\underline{H}$C(CH$_3$)$_2$], 3.2–3.5 [C$\underline{H}_2$NH], 3.5–3.7 [OCH$_3$ and C$\underline{H}_2$OH], 3.8–4.6 [CH$_2$OAr, CH$_2$OCONH, CH$_2$OCOC], 5.2–5.6 [NH], 6.7–7.2 [CH$_{Ar}$].

2nd stage: synthesis of poly(MMA-co-IPPECEM) 1:1 with sulfone end group (P(MMA-co-IPPECEM)-SO$_2$—R)

3 g (contain 0.5 mmol thioether groups) of P(MMA-IPPECEM)-SR was dissolved in 20 ml methylene chloride and the solution was cooled to −5° C. 10 ml ethanol and 0.346 g (0.70 mmol) magnesium monoperoxyphthalate hexahydrate were added and the reaction mixture was stirred for 18 h at room temperature. Then, the solvent was separated off in a fine vacuum and the white solid was dissolved in 3 ml acetonitrile. The solution was slowly added dropwise to 300 ml methanol at 0° C. The precipitated polymer solid was filtered off and dried to constant weight at 60° C. in a fine vacuum. 1.79 g (60% yield) of P(MMA-IPPECEM)-SO$_2$—R was obtained as a white solid.

$^1$H-NMR (CDCl$_3$, 400 MHz): δ (ppm)=0.7–1.1 [CH$_3$CCO], 1.1–1.3 [(CH$_3$)$_2$CH], 1.5–2.2 [CH$_2$C], 2.8–2.9 [HC(CH$_3$)$_2$], 3.0–3.2 [br. CH$_2$SO$_2$], 3.2–3.5 [CH$_2$NH], 3.5–3.7 [OCH$_3$ and CH$_2$OH], 3.8–4.6 [CH$_2$OAr, CH$_2$OCONH, CH$_2$OCOC], 5.2–5.6 [NH], 6.7–7.2 [CH$_{Ar}$].

3$^{rd}$ stage: peroxidation of P(MMA-co-IPPECEM)-SO$_2$—R) to form PCHP-5

1.5 g (contain 3.3 mmol isopropyl groups) of P(MMA-IPPECEM)-SO$_2$—R, 0.027 g (0.17 mmol) N-hydroxyphthalimide and 0.033 g (0.2 mmol) AIBN were dissolved in 15 ml acetonitrile. The resulting solution was heated to 55° C. and a light air flow was passed through the solution. 0.087 g (0.53 mmol) AIBN was added every 24 h. After 96 h reaction time, the reaction was tracked by means of $^1$H-NMR spectroscopy, the solution was cooled to room temperature and slowly added dropwise to 200 ml cold water (4° C.). After the solution had been filtered, the solid formed was dissolved in 15 ml acetonitrile. This solution was then again added dropwise to 200 ml cold water and thus the polymer precipitated out again. The reprepitation was repeated once more. The colourless solid formed was dried in a freeze dryer. 1.0 g (66% yield) of PCHP-5 was obtained as a white powder. 85% of the isopropyl groups had been successfully converted into the corresponding hydroperoxide groups. A number-average molar mass M$_n$ of 6000 g/mol was determined in THF by means of GPC, wherein n~11.

$^1$H-NMR (CDCl$_3$, 400 MHz): δ (ppm)=0.7–1.1 [CH$_3$CCO], 1.1–1.3 [(CH$_3$)$_2$CH$_{radicals}$], 1.5–2.2 [CH$_3$)$_2$C and CH$_2$C], 2.8–2.9 [HC(CH$_3$)$_2$ radicals], 3.0–3.2 [br. CH$_2$SO$_2$], 3.2–3.5 [CH$_2$NH], 3.5–3.7 [OCH$_3$ and CH$_2$OH], 3.8–4.6 [CH$_2$OAr, CH$_2$OCONH, CH$_2$OCOC], 5.2–5.6 [NH], 6.7–7.4 [CH$_{Ar}$].

Example 8

Composite Cements Based on the Polymeric Hydroperoxides PCHP-1, PCHP-2 and PCHP-4 from Examples 3, 4 and 6

3 catalyst pastes (cat. pastes) A, B and C were prepared from a mixture of the dimethacrylates bis-GMA (an addition product of methacrylic acid and bisphenol A diglycidyl ether), UDMA (an addition product of 2-hydroxyethyl methacrylate and 2,2,4-trimethylhexamethylene-1,6-diisocyanate), triethylene glycol dimethacrylate (TEGDMA), the stabilizer MEHQ (hydroquinone monomethyl ether), the initiator components PCHP-1, PCHP-2 or PCHP-4 from Examples 3, 4 and 6 and the filler silanized barium aluminium silicate glass GM 27884 (0.7 µm, Schott) (Table 1).

TABLE 1

Composition of the cat. pastes A-C

| Component | Cat. paste A | Cat. paste B | Cat. paste C |
| --- | --- | --- | --- |
| Bis-GMA | 9.445 | 9.445 | 9.445 |
| UDMA | 12.592 | 12.592 | 12.592 |
| TEGDMA | 9.445 | 9.445 | 9.445 |
| MEHQ | 0.018 | 0.018 | 0.018 |
| PCHP-1 | 3.500 | — | — |
| PCHP-2 | — | 3.500 | — |
| PCHP-4 | — | — | 3.500 |
| GM 27884 | 65.00 | 65.00 | 65.00 |

The base paste A was prepared from a mixture of the dimethacrylates bis-GMA, UDMA, TEGDMA, the stabilizers MEHQ (hydroquinone monomethyl ether) and TEMPO (2,2,6,6-tetramethylpiperidinyloxyl), the initiator components copper(II) acetylacetonate (Cu(acac)$_2$) and acetylthiourea (ATU) and the filler silanized barium aluminium silicate glass GM 27884 (0.7 µm, Schott) (Table 2).

TABLE 2

Composition of the base paste A (data in % by mass)

| Component | Base paste A |
| --- | --- |
| Bis-GMA | 10.323 |
| UDMA | 13.764 |
| TEGDMA | 10.323 |
| TEMPO | 0.007 |
| MEHQ) | 0.018 |
| Cu(acac)$_2$ | 0.007 |
| ATU | 0.555 |
| GM 27884 | 65.00 |

Chemically curing composite cements consisting in each case of a cat. paste (A to C) and the base paste A were prepared. The flexural strength and the flexural modulus of elasticity were determined according to the EN ISO-4049 standard (2019, Dentistry—Polymer-based filling, restorative and luting materials). The mechanical properties were measured after 24 h storage of the test pieces in water (WS) at 37° C. (Table 3). The processing time (PT) of the resin pastes was determined by means of a Motion Compact Rheometer (MCR 302 Anton Paar). In the process, the base and cat. pastes were blended in each case by hand on a mixing block in a 1:1 ratio. The material was then applied to a die consisting of Delrin with a roughened surface on the MCR rheometer. A measuring bob shaft secured on a spindle with a likewise roughened surface compresses the sample and with slight rotation determines the storage modulus. At the beginning of the stable phase and after achieving a particular gradient, an inflection point was defined in each case. The inflection points were then connected by a straight line. From this straight line, the measurement point furthest away was defined as PT. The whole measurement was carried out at 28.7° C. in a temperature-controlled chamber.

TABLE 3

Flexural strength (FS, MPa), flexural modulus of elasticity (FM, MPa) and processing time (PT, s) of the cements made from cat. pastes A-C and base paste A

| Component | FS 24 h 37° C. H$_2$O (MPa) | FM 24 h 37° C. H$_2$O (MPa) | PT(s) |
| --- | --- | --- | --- |
| Cat. paste A + base paste A | 89.5 ± 8.2 | 6289 ± 327 | 157 ± 11 |
| Cat. paste B + base paste A | 102.2 ± 11.2 | 6847 ± 144 | 113 ± 2 |
| Cat. paste C + base paste A | 87.8 ± 7.8 | 6229 ± 610 | 149 ± 2 |

The results in Table 3 prove a good curing with processing times of 113–157 s, wherein the PT should lie in the range of from 1–3 min. The cements obtained exhibit good mechanical properties.

The invention claimed is:

1. A cumene hydroperoxide oligomer according to Formula (I):

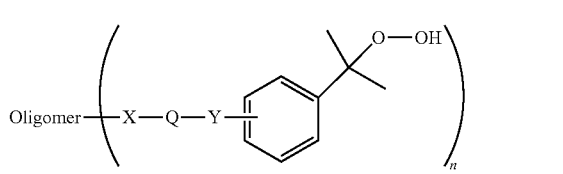

Formula I in which the variables have the following meanings:
OLIGOMER (meth)acrylate- or styrene-based copolymer chain, which is substituted n times by the group which is in brackets,
Q a divalent, linear or branched aliphatic $C_1$-$C_{10}$ radical, which can be interrupted by 1 to 3 O atoms and can carry 1 to 3 OH or $OR^2$ substituents, wherein $R^2$ is an aliphatic, linear or branched $C_1$-$C_5$ alkyl radical,
X, Y independently of each other are absent, an ether, ester or urethane group, wherein the substitution on the aromatic compound is effected in position 4 relative to the cumene hydroperoxide group, and
n a value from 5 to 20, and
wherein the cumene hydroperoxide oligomer has a number-average molar mass of from 1,000 to 10,000 g/mol.

2. The cumene hydroperoxide oligomer according to claim 1, which has the following structure:

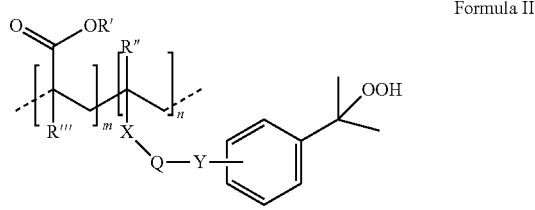

Formula II in which
R' is a linear or branched $C_1$-$C_{10}$ alkyl radical, which can be substituted by one or more functional groups comprising —OH, —COOH and/or —Cl, or is unsubstituted, or a cyclic $C_4$-$C_{10}$ alkyl radical, a heterocyclic or isocyclic aromatic $C_4$-$C_6$ hydrocarbon radical,
R",R'" independently of each other in each case are H or methyl,
m is a number from 0 to 30,
n is a number from 5 to 20, and
the remaining variables have the meanings named in claim 1.

3. The cumene hydroperoxide oligomer according to claim 2, in which the ratio of n to m lies in a range of from 0.1 to 0.9.

4. The cumene hydroperoxide oligomer according to claim 1, which has a number-average molar mass of from 1,000 to 6,000 g/mol.

5. A radically polymerizable composition, which comprises at least one cumene hydroperoxide oligomer according to claim 1, at least one thiourea derivative and at least one radically polymerizable monomer.

6. The composition according to claim 5, which comprises as thiourea derivative acetyl-, allyl-, pyridyl-, phenyl-thiourea, hexanoylthiourea or a mixture thereof.

7. The composition according to claim 5, which comprises as radically polymerizable monomer at least one mono- and/or multifunctional (meth)acrylate.

8. The composition according to claim 7, which comprises as radically polymerizable monomer
bisphenol A dimethacrylate, bis-GMA (an addition product of methacrylic acid and bisphenol A diglycidyl ether), ethoxylated or propoxylated bisphenol A dimethacrylate, 2-[4-(2-methacryloyloxyethoxyethoxy)phenyl]-2-[4-(2-methacryloyloxyethoxy)phenyl]propane, 2,2-bis[4-(2-methacryloxypropoxy)phenyl]propane, UDMA (an addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), di-, tri- or tetraethylene glycol dimethacrylate, trimethylolpropane trimethacrylate, pentaerythritol tetramethacrylate, glycerol di- and trimethacrylate, 1,4-butanediol dimethacrylate, 1,10-decanediol dimethacrylate ($D_3MA$), bis(methacryloyloxymethyl)tricyclo-[5.2.1.02,6]decane (DCP), a polyethylene glycol or polypropylene glycol dimethacrylate, polyethylene glycol 200 dimethacrylate, polyethylene glycol 400 dimethacrylate (PEG 200 DMA or PEG 400 DMA), 1,12-dodecanediol dimethacrylate or a mixture thereof and/or
benzyl and furfuryl methacrylate, 2-phenoxyethyl methacrylate, 2-(o-biphenyloxy)ethyl methacrylate, 2-hydroxy-3-phenoxypropyl methacrylate, phenethyl methacrylate, 2-[(benzyloxycarbonyl)-amino]-ethyl methacrylate, 2-[(benzylcarbamoyl)oxy]-ethyl methacrylate, 1-phenoxypropan-2-yl methacrylate and 2-(p-cumylphenoxy)-ethyl methacrylate, tricyclodecane methacrylate, tricyclodecane methyl methacrylate and/or 2-(p-cumylphenoxy)ethyl methacrylate.

9. The composition according to claim 5, which additionally comprises a transition metal compound.

10. The composition according to claim 9, wherein the transition metal compound comprises copper, iron, cobalt, nickel, manganese or a mixture thereof.

11. The composition according to claim 5, which additionally comprises at least one organic or inorganic filler.

12. The composition according to claim 11, wherein the at least one organic or inorganic filler comprises one or more of an oxide comprising $SiO_2$, $ZrO_2$ and $TiO_2$ or a mixed oxide of $SiO_2$, $ZrO_2$, ZnO and/or $TiO_2$, a nanoparticulate or microfine filler comprising fumed silica or precipitated silica, glass powder comprising quartz, glass ceramic or radiopaque glass powder comprising barium or strontium aluminium silicate glass powder, a radiopaque filler comprising ytterbium trifluoride, tantalum(V) oxide, barium sulfate, a mixed oxide of $SiO_2$ with ytterbium(III) oxide or tantalum(V) oxide, a ground prepolymer or a pearl polymer.

13. The composition according to claim 5, which comprises
(a) 0.5 to 15 wt.- % of at least one cumene hydroperoxide oligomer of Formula I,
(b) 0.01 to 5 wt.- % of at least one thiourea derivative,
(c) 50 to 95 wt.- % of at least one radically polymerizable monomer,
(d) 0 to 80 wt.- % filler(s) and
(e) 0.001 to 5 wt.- % additive(s),
in each case relative to the total mass of the composition.

14. The composition according to claim 5, which comprises
(a) 1.0 to 12.0 wt.- %, of at least one cumene hydroperoxide oligomer of Formula I,
(b) 0.05 to 2.0 wt.- %, of at least one thiourea derivative,
(c) 10 to 95 wt.- %, of at least one radically polymerizable monomer,
(d) 10 to 80 wt.- %, filler(s) and
(e) 0.01 to 3 wt.- %, additive(s),
in each case relative to the total mass of the composition.

15. The composition according to claim 5, for the therapeutic treatment of damaged teeth as dental cement, filling composite or veneering material.

16. A process for non-therapeutic production or repair of dental restorations comprising prostheses, artificial teeth, inlays, onlays, crowns, bridges and complete dentures, comprising the use of the composition according to claim 5 for the production or repair of the dental restorations.

17. A process for use of a cumene hydroperoxide oligomer as initiator for radical polymerization, comprising initiating the radical polymerization with the cumene hydroperoxide oligomer of claim 1.

18. The cumene hydroperoxide oligomer according to claim 1, which has the following structure:
in which

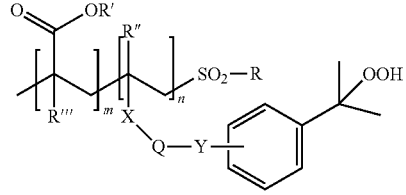

Formula IIa

R is a branched or linear C2-C15 alkyl radical, which can be substituted by one or more functional groups comprising —Br, —Cl, —OH and/or —COOH and/or —Cl, or is unsubstituted, R' is a linear or branched C1-C10 alkyl radical, which can be substituted by one or more functional groups comprising —OH, —COOH and/or —Cl, or is unsubstituted, or a cyclic C4-C10 alkyl radical, a heterocyclic or isocyclic aromatic C4-C6 hydrocarbon radical, R",R'" independently of each other in each case are H or methyl, m is a number from 0 to 30, n is a number from 5 to 20, and the remaining variables have the meanings named in claim 1.

* * * * *